United States Patent
Yokoyama et al.

(10) Patent No.: US 8,227,757 B2
(45) Date of Patent: Jul. 24, 2012

(54) RADIOGRAPHIC IMAGING APPARATUS AND RADIOGRAPHIC IMAGING SYSTEM, CONTROL METHOD THEREFOR, AND PROGRAM THEREFOR

(75) Inventors: Keigo Yokoyama, Honjo (JP); Tadao Endo, Honjo (JP); Toshio Kameshima, Kumagaya (JP); Masayoshi Akiyama, Kumagaya (JP); Tomoyuki Yagi, Honjo (JP); Katsuro Takenaka, Honjo (JP); Sho Sato, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/844,554

(22) Filed: Jul. 27, 2010

(65) Prior Publication Data

US 2011/0024641 A1   Feb. 3, 2011

Related U.S. Application Data

(63) Continuation of application No. PCT/JP2009/061610, filed on Jun. 25, 2009.

(51) Int. Cl.
  *G01T 1/00* (2006.01)
  *G01J 1/42* (2006.01)
(52) U.S. Cl. .................... 250/354.1; 250/393
(58) Field of Classification Search ............... 250/354.1, 250/393
  See application file for complete search history.

(56) References Cited

U.S. PATENT DOCUMENTS

| 7,170,973 | B2 * | 1/2007 | Gipp et al. | 378/98.8 |
| 2004/0183025 | A1 * | 9/2004 | Sato | 250/370.11 |
| 2005/0238139 | A1 | 10/2005 | Gipp et al. | |
| 2007/0131843 | A1 | 6/2007 | Yokoyama et al. | |
| 2008/0232549 | A1 | 9/2008 | Poorter | |
| 2009/0250592 | A1 | 10/2009 | Takeda et al. | |
| 2009/0283685 | A1 | 11/2009 | Takeda et al. | |
| 2010/0054401 | A1 * | 3/2010 | Blendl et al. | 378/37 |

FOREIGN PATENT DOCUMENTS

| JP | 59-178877 A | 10/1984 |
| JP | 7059010 A | 3/1995 |
| JP | 11-128213 A | 5/1999 |
| JP | 3275803 B2 | 4/2002 |
| JP | 2005-524466 T | 8/2005 |
| JP | 2007-185493 A | 7/2007 |
| JP | 2007-225598 A | 9/2007 |
| JP | 2008-134237 A | 6/2008 |
| JP | 2008-167846 A | 7/2008 |
| JP | 2009-504221 T | 2/2009 |

* cited by examiner

*Primary Examiner* — David Porta
*Assistant Examiner* — Carolyn Igyarto
(74) *Attorney, Agent, or Firm* — Canon U.S.A., Inc. IP Division

(57) ABSTRACT

An imaging apparatus includes a detector, having a plurality of pixels arranged in a matrix, for performing first and second radiography operations, a bias light source, and a control unit that controls the operation of the detector and the bias light source. In the first radiography operation, image data corresponding to radiation in a first radiation field corresponding to some of the pixels is output. In the second radiography operation, image data corresponding to radiation in a second radiation field larger than the first radiation field is output. In accordance with a change from the first radiation field to the second radiation field, the operation of the bias light source is controlled so that the irradiation with the bias light is performed during a period between the first and second radiography operations at a bias-light integral dose determined based on radiation integral dose information in the first radiography operation.

14 Claims, 16 Drawing Sheets

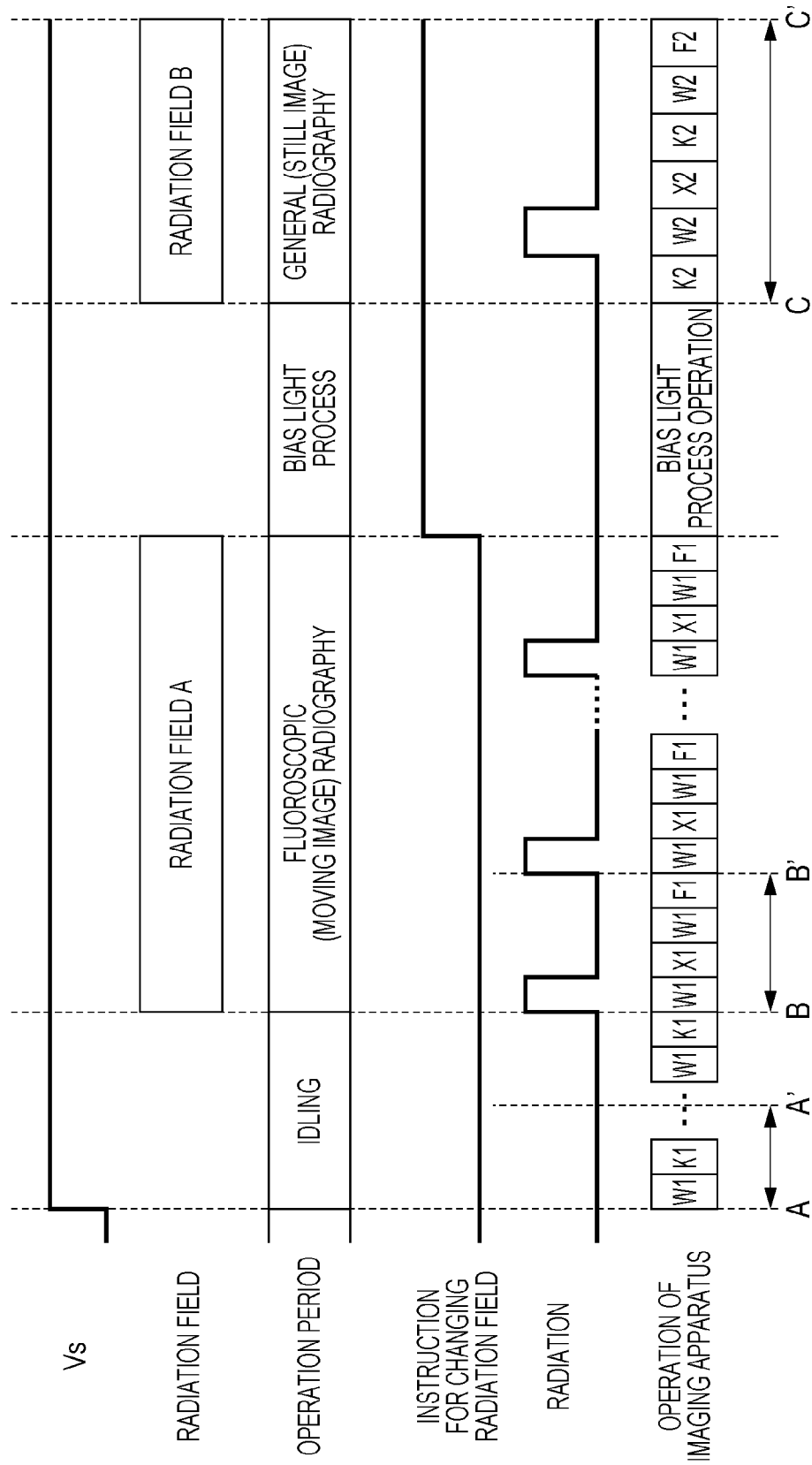

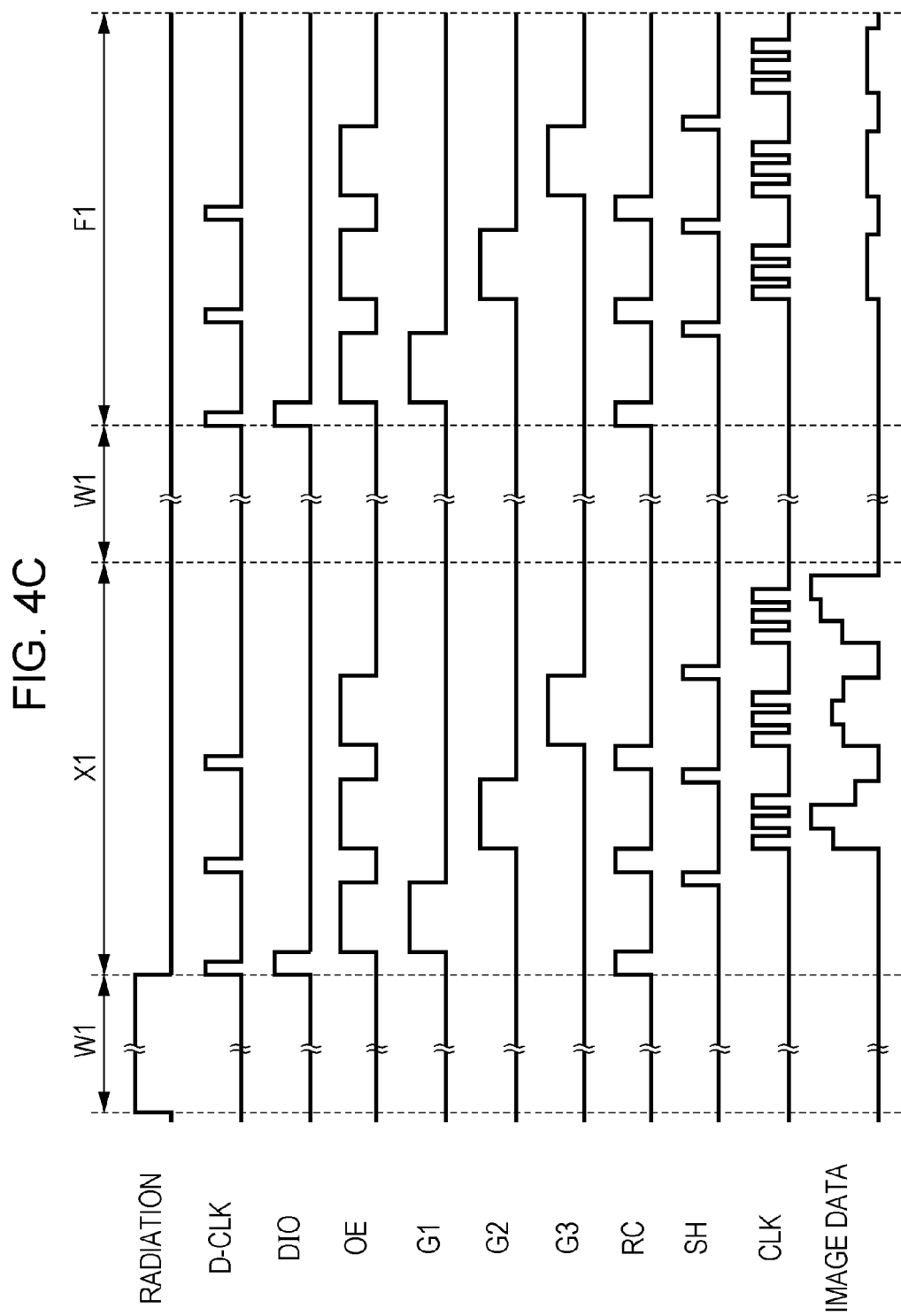

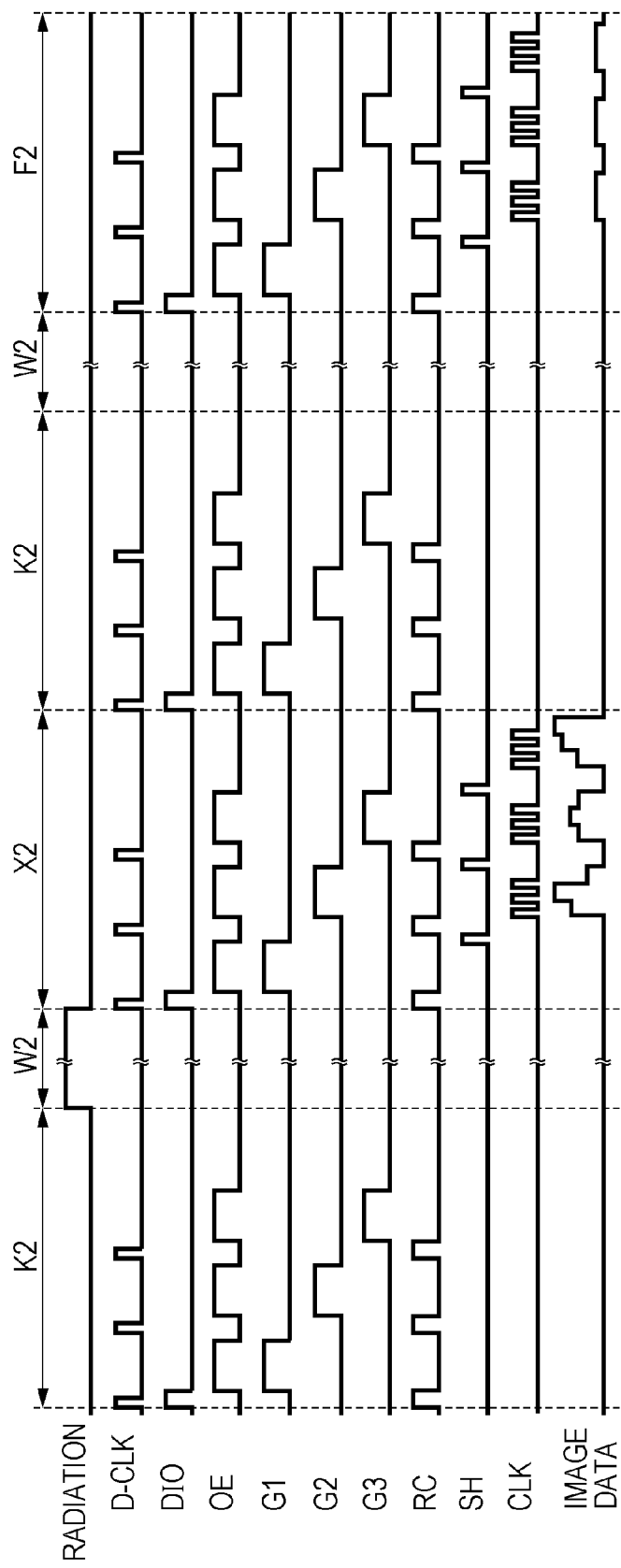

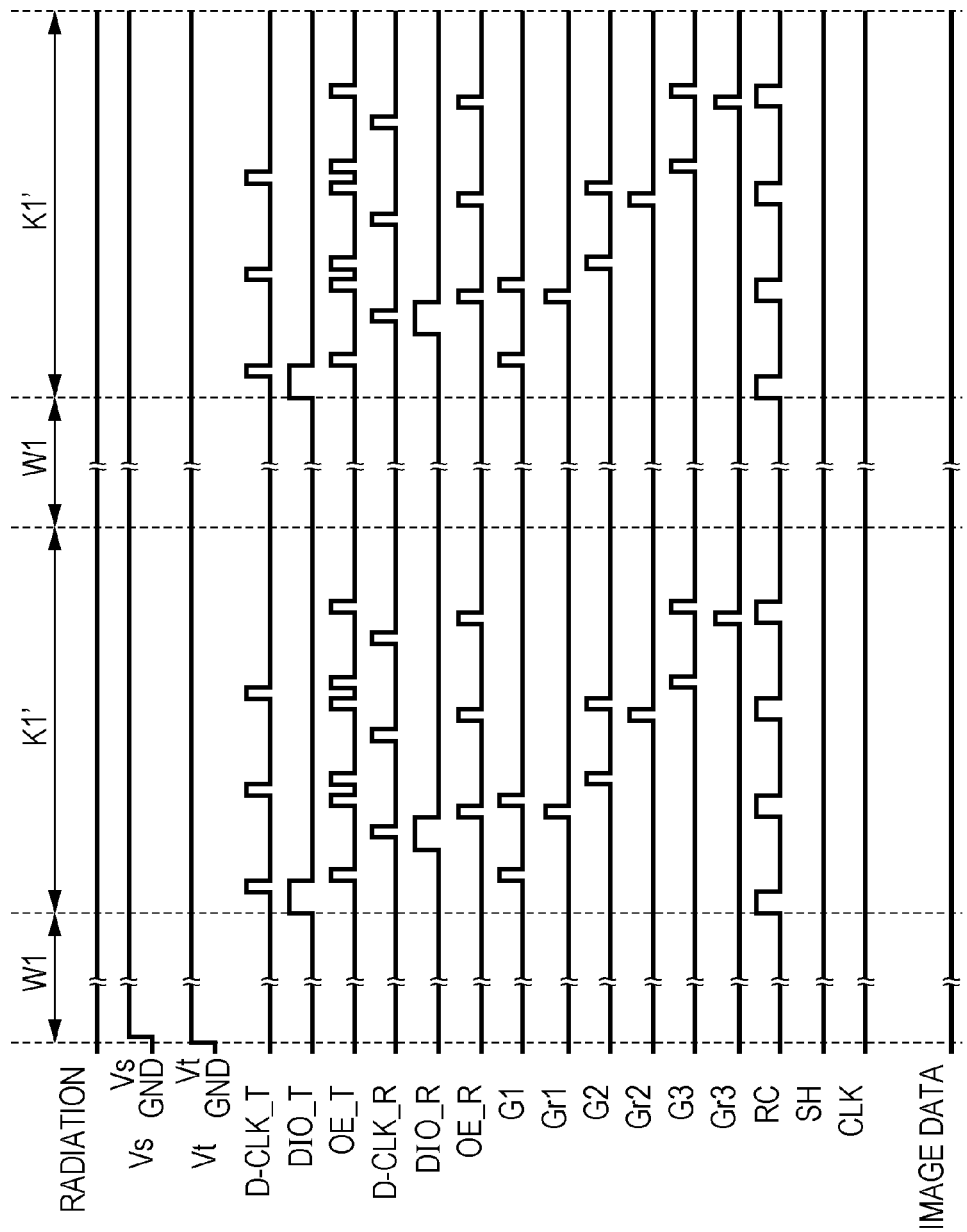

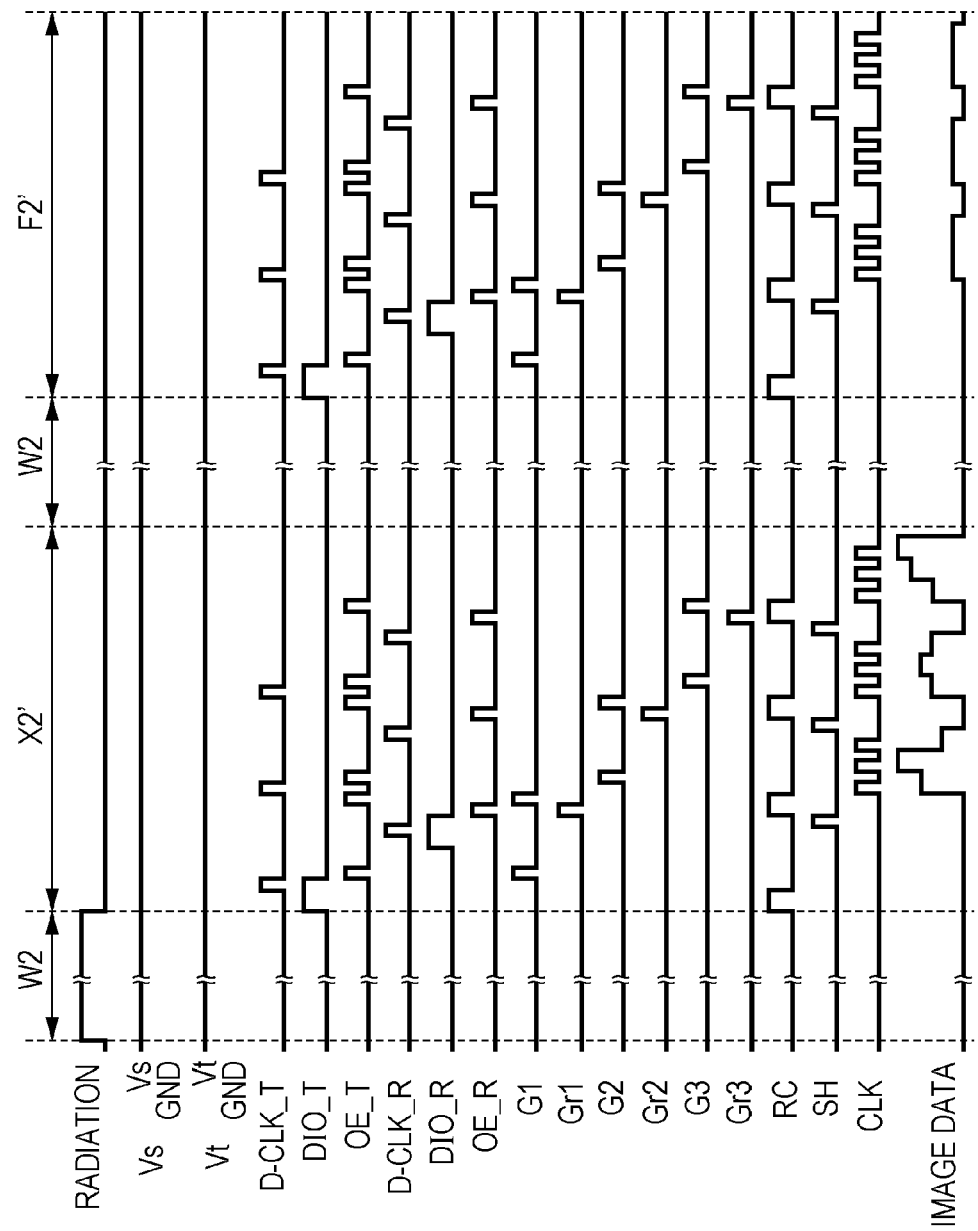

RADIOGRAPHIC IMAGING APPARATUS AND RADIOGRAPHIC IMAGING SYSTEM, CONTROL METHOD THEREFOR, AND PROGRAM THEREFOR

CROSS-REFERENCE TO RELATED APPLICATIONS

This application is a Continuation of International Application No. PCT/JP2009/061610, filed Jun. 25, 2009, which is hereby incorporated by reference herein in its entirety.

BACKGROUND OF THE INVENTION

1. Technical Field

The present invention relates to an imaging apparatus, a radiographic imaging apparatus, and a radiographic imaging system. More specifically, the present invention relates to an imaging apparatus used in a radiographic imaging apparatus and a radiographic imaging system, which is suitable for use in still image radiography such as general radiography or moving image radiography such as fluoroscopic radiography in medical diagnosis. Note that, in the present invention, the term radiation includes, in addition to α rays, β rays, γ rays, which are beams of particles (including photons) emitted by a radiation decay, beams having energy higher than or equal to that of the above rays, for example, X-rays, particle beams, cosmic rays, and others.

2. Background Art

In recent years, radiographic imaging apparatuses including a flat panel detector (hereinafter abbreviated as FPD) formed of a semiconductor material have begun to be put into practice as radiographic apparatuses used for X-ray medical diagnostic imaging or non-destructive inspection. Such radiographic imaging apparatuses are used as, for example, in medical diagnostic imaging, digital imaging apparatuses for still image radiography like general radiography or moving image radiography like fluoroscopic radiography.

In such radiographic imaging apparatuses, as disclosed in PTL 1, the ability to switch between an area (field-of-view size) that is read by an FPD and a radiation area of X-rays has been studied. However, in a case where switching is performed so as to increase the radiation area, the sensitivity or dark output of pixels differs between the irradiated area and the non-irradiated area of the FPD. Thus, a ghost (image step), which is affected by the radiation area, occurs in an obtained image, leading to the risk of reduced image quality.

In PTL 2, an examination is made of performing image processing for correction on such a ghost that is affected by the radiation area. Specifically, required ghost correction coefficients are obtained for each X-ray irradiation condition on the basis of data that includes a ghost and that is obtained by uniform irradiation, the ghost correction coefficients corresponding to X-ray irradiation conditions under which data regarding the part being examined, which is the radiation area, is collected and the time taken from the start of X-ray irradiation. Thus, the data regarding the part being examined is corrected using the required ghost correction coefficients, and corrected image data is generated.

In the correction technique of PTL 2, however, since the correction is performed using image processing, the management of parameters or correction processing is complicated and the complexity of the overall apparatus increases. In addition, complex operations such as acquiring data in advance for correction are required, and also strict management such as thoroughgoing data sampling is required to obtain stable image quality. Further, the number of afterimages included in an image signal obtained from the FPD, which may cause the ghosts described above, is not reduced, and therefore it is difficult to obtain optimum effects in various situations.

Citation List

Patent Literature (PTL)

PTL 1: Japanese Patent Application Laid-Open No. 11-128213

PTL 2: Japanese Patent Application Laid-Open No. 2008-167846

SUMMARY OF INVENTION

As a result of intensive studies to provide an imaging apparatus and system capable of reducing the occurrence of an image step affected by a radiation area, which can occur in an obtained image, and avoiding significant reduction in image quality without performing complex image processing, the inventor of the claimed invention has achieved the following aspects of the invention.

An imaging system according to the present invention is a radiographic imaging system including an imaging apparatus including a detector for performing a radiography operation for outputting image data corresponding to emitted radiation or light, the detector having a plurality of pixels arranged in a matrix, the pixels having conversion elements that convert radiation or light into electric charge, a bias light source that irradiates the detector with bias light different from the radiation or light, and a control unit for controlling an operation of the detector including the radiography operation and an operation of the bias light source; and a control computer that controls the imaging apparatus, wherein the radiography operation includes a first radiography operation for outputting image data corresponding to radiation or light with which the detector is irradiated in a first radiation field corresponding to some pixels included in the plurality of pixels, and a second radiography operation for outputting image data corresponding to radiation or light with which the detector is irradiated in a second radiation field larger than the first radiation field, wherein the control computer determines an integral dose of the bias light on the basis of information regarding an integral dose of radiation in the first radiography operation, and applies a control signal based on the determined integral dose of the bias light to the control unit, and wherein the control unit controls the operation of the bias light source so that, in accordance with a change from the first radiation field to the second radiation field, the irradiation with the bias light is performed at the determined integral dose of the bias light during a period between the first radiography operation and the second radiography operation.

An imaging apparatus according to the present invention is an imaging apparatus including a detector for performing a radiography operation for outputting image data corresponding to emitted radiation or light, the detector having a plurality of pixels arranged in a matrix, the pixels having conversion elements that convert radiation or light into electric charge, a bias light source that irradiates the pixels with bias light different from the radiation or light, and a control unit for controlling an operation of the detector including the radiography operation and an operation of the bias light source, wherein the radiography operation includes a first radiography operation for outputting image data corresponding to radiation or light with which the detector is irradiated in a first radiation field corresponding to some pixels included in the plurality of pixels, and a second radiography operation for outputting image data corresponding to radiation or light with which the detector is irradiated in a second radiation field larger than the first radiation field, and wherein the control unit controls the operation of the bias light source so that, in accordance with a change from the first radiation field to the second radiation field, the irradiation with the bias light is performed at an integral dose of the bias light, which is determined on the basis of information regarding an integral dose of radiation in the first radiography operation, during a period between the first radiography operation and the second radiography operation.

A control method according to the present invention is a control method for an imaging apparatus including a detector for performing a radiography operation for outputting image data corresponding to emitted radiation or light, the detector having a plurality of pixels arranged in a matrix, the pixels having conversion elements that convert radiation or light into electric charge, and a bias light source that irradiates the pixels with bias light different from the radiation or light, the imaging apparatus controlling an operation of the detector including the radiography operation and an operation of the bias light source, the control method including performing a first radiography operation for outputting image data corresponding to radiation or light with which the detector is irradiated in a first radiation field corresponding to some pixels included in the plurality of pixels; determining an integral dose of the bias light on the basis of information regarding an integral dose of radiation in the first radiography operation; in accordance with an instruction for changing from the first radiation field to a second radiation field larger than the first radiation field, performing the irradiation with the bias light at the determined integral dose of the bias light during a period between the first radiography operation and the second radiography operation; and performing a second radiography operation for outputting image data corresponding to radiation or light with which the detector is irradiated in the second radiation field after the irradiation with the bias light.

A computer-readable medium that stores therein a computer-executable program according to the present invention is a program for causing a computer to execute control of an imaging apparatus including a detector for performing a radiography operation for outputting image data corresponding to emitted radiation or light, the detector having a plurality of pixels arranged in a matrix, the pixels having conversion elements that convert radiation or light into electric charge, and a bias light source that irradiates the pixels with bias light different from the radiation or light, the imaging apparatus controlling an operation of the detector including the radiography operation and an operation of the bias light source, the program causing the computer to execute control of performing a first radiography operation for outputting image data corresponding to radiation or light with which the detector is irradiated in a first radiation field corresponding to some pixels included in the plurality of pixels; control of determining an integral dose of the bias light based on information regarding an integral dose of radiation in the first radiography operation; control of, in accordance with an instruction for changing from the first radiation field to a second radiation field larger than the first radiation field, performing the irradiation with the bias light at the determined integral dose of the bias light during a period between the first radiography operation and the second radiography operation; and control of performing a second radiography operation for outputting image data corresponding to radiation or light with which the detector is irradiated in the second radiation field after the irradiation with the bias light.

Further features of the present invention will become apparent from the following description of exemplary embodiments with reference to the attached drawings.

BRIEF DESCRIPTION OF DRAWINGS

FIG. 4A is a timing chart describing the operation of an imaging apparatus and an imaging system of the present invention.

FIG. 4C is a timing chart describing the operation of the imaging apparatus and the imaging system of the present invention.

FIG. 4D is a timing chart describing the operation of the imaging apparatus and the imaging system of the present invention.

FIG. 7A is a timing chart describing the operation of another imaging apparatus and imaging system according to the present invention.

FIG. 7C is a timing chart describing the operation of the other imaging apparatus and imaging system according to the present invention.

DESCRIPTION OF EMBODIMENTS

Figure 1:
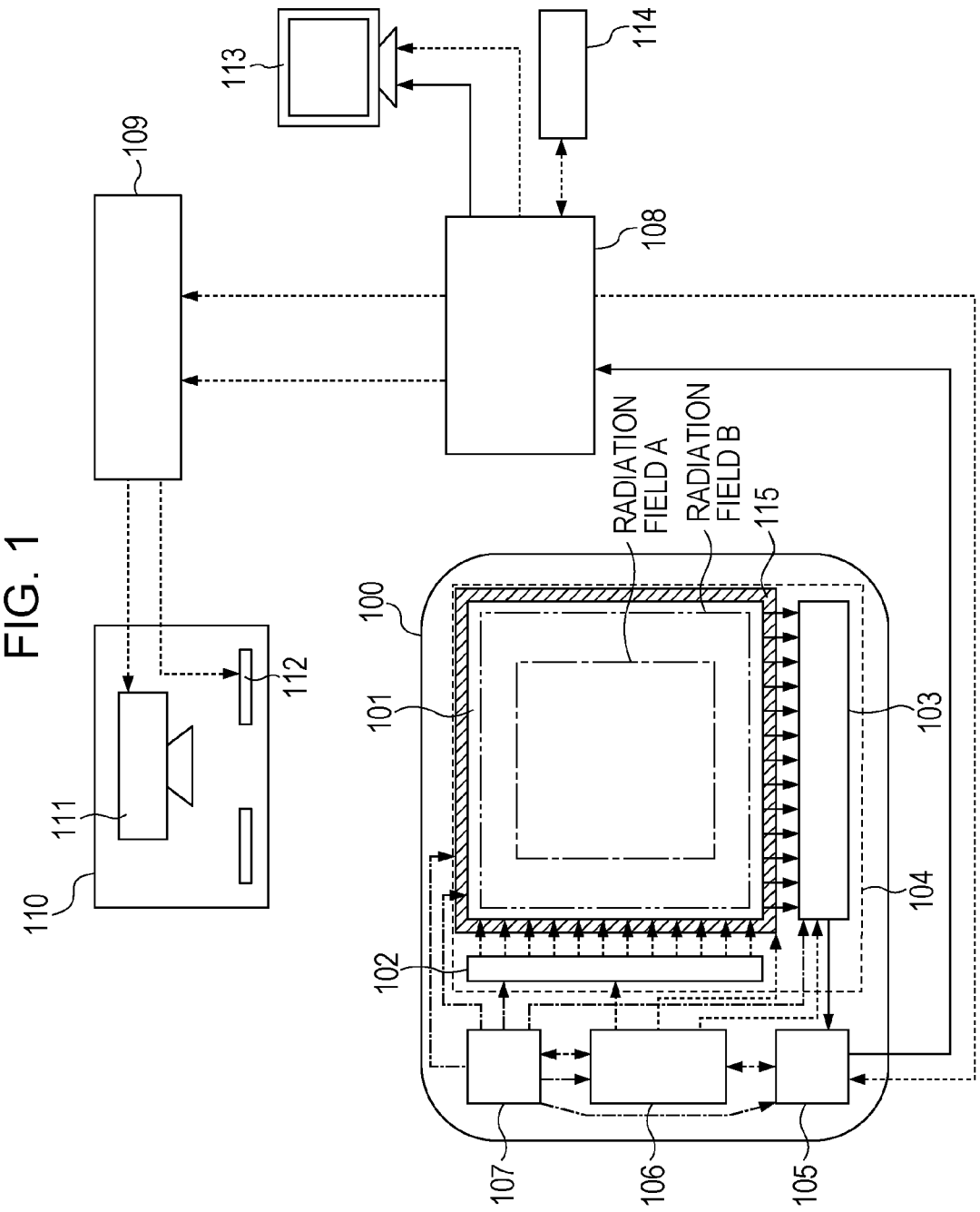
FIG. 1 is a conceptual block diagram of an imaging system including an imaging apparatus according to the present invention.

An embodiment to which the present invention is suitably applicable will be described in detail hereinafter with reference to the drawings. A radiographic imaging system of the present embodiment illustrated in FIG. 1 includes an imaging apparatus 100, a control computer 108, a radiation control device 109, a radiation generating device 110, a display device 113, and a console 114. The imaging apparatus 100 includes a FPD (flat panel detector) 104 including a detection unit 101 having a plurality of pixels that convert radiation or light into electrical signals, a drive circuit 102 that drives the detection unit 101, and a read circuit 103 that outputs the electrical signals from the driven detection unit 101 as image data. The imaging apparatus 100 further includes a signal processing unit 105 that processes the image data from the FPD 104 and that outputs a result, and a control unit 106 that supplies a control signal to each constituent element and that controls the operation of the FPD 104 and a bias light source 115 described below. The imaging apparatus 100 further includes a power supply unit 107 that supplies a bias to each constituent element and the bias light source 115. The imaging apparatus 100 further includes the bias light source 115 that irradiates the FPD 104 with bias light separate from radiation generated from a radiation source 111 described below or light converted from the radiation by a wavelength converter described below. The signal processing unit 105 receives a control signal from a control computer 108 described below, and provides the control unit 106 with the control signal. The power supply unit 107 incorporates therein a power supply circuit such as a regulator or an inverter that receives a voltage from an external power source or built-in battery (not illustrated) and that supplies voltages required for the detection unit 101, the drive circuit 102, the read circuit 103, and the bias light source 115. The bias light source 115 is provided so as to face a surface (back side) of a substrate on which the detection unit 101 is provided, which is opposite to a light receiving surface on which pixels described below are provided, and is arranged so as to irradiate the overall detection unit 101 with bias light from the back side. Here, the bias light source 115 is arranged so as to be able to irradiate an area equivalent to or larger than a radiation field B of the detection unit 101, described below, with bias light.

The control computer 108 performs image processing for synchronization between the radiation generating device 110 and the imaging apparatus 100, transmission of a control signal for determining the state of the imaging apparatus 100, and correction or storage/display of image data from the imaging apparatus 100. The control computer 108 further transmits a control signal for determining radiation irradiation conditions on the basis of information from the console 114 to the radiation control device 109.

The radiation control device 109 receives a control signal from the control computer 108, and controls the operation for emitting radiation from the radiation source 111 incorporated in the radiation generating device 110 or the operation of a radiation field aperture mechanism 112. The radiation field aperture mechanism 112 has a function capable of changing a given radiation field that is an area irradiated with radiation or light corresponding to the radiation in the detection unit 101 of the FPD 104, and, in the present embodiment, has a function capable of switching between a radiation field A and the radiation field B. The radiation field A, which serves as a first radiation field in the present invention, is irradiated with radiation corresponding to some pixels included in the plurality of pixels, for example, when the total number of pixels is approximately 2800 rows by approximately 2800 columns, pixels of approximately 1000 rows by approximately 1000 columns. Also, the radiation field B, which serves as a second radiation field in the present invention, is irradiated with radiation corresponding to an area larger than the radiation field A, for example, all the pixels. The console 114 allows information about the object being examined or radiographic conditions to be input as parameters for various types of control performed by the control computer 108, and transmits the input results to the control computer 108. The display device 113 displays the image data subjected to image processing by the control computer 108.

Next, an imaging apparatus according to a first embodiment of the present invention will be described with reference to FIG. 2. Elements having the same configuration as that described with reference to FIG. 1 are assigned the same numerals, and detailed descriptions thereof are omitted. Further, in FIG. 2, an imaging apparatus including an FPD having pixels of three rows by three columns is illustrated for ease of description. In actuality, however, an imaging apparatus has a larger number of pixels. For example, a 17-inch imaging apparatus has pixels of approximately 2800 rows by approximately 2800 columns.

The detection unit 101 has a plurality of pixels arranged in a matrix. Each of the pixels has a conversion element 201 that converts radiation or light into electric charge, and a switch element 202 that outputs an electrical signal corresponding to the electric charge. In the present embodiment, a PIN-type photodiode that is arranged on an insulating substrate such as a glass substrate and that contains amorphous silicon as a main component is used as a photoelectric conversion element that converts light with which the conversion element is irradiated into electric charge. An indirect-type conversion element provided with a wavelength converter on the radiation incident side of the above photoelectric conversion element, which converts radiation into light of a wavelength band detectable by the photoelectric conversion element, or a direct-type conversion element that converts radiation directly into electric charge is suitably used as a conversion element. A transistor having a control terminal and two main terminals is suitably used as the switch element 202. In the present embodiment, a thin film transistor (TFT) is used. One electrode of the conversion element 201 is electrically connected to one of the two main terminals of the switch element 202, and the other electrode is electrically connected to a bias power supply 107a via a common bias line Bs. A plurality of switch elements in the row direction, for example, T11 to T13, have control terminals that are commonly electrically connected to a drive line G1 in the first row, and drive signals for controlling the conductive state of the switch elements are applied from the drive circuit 102 via drive lines on a row-by-row basis. In a plurality of switch elements in the column direction, for example, T11 to T31, the other main terminals are electrically connected to a signal line Sig1 in the first column, and electrical signals corresponding to the electric charge of the conversion elements are output to the read circuit 103 via signal lines during a period during which the switch elements are in a conductive state. A plurality of signal lines Sig1 to Sig3 arranged in the column direction carry the electrical signals output from the plurality of pixels to the read circuit 103 in parallel.

The read circuit 103 is provided with, for the respective signal lines, amplifier circuits 207 that amplify the electrical signals output in parallel from the detection unit 101. Further, each amplifier circuit 207 includes an integrating amplifier 203 that amplifies an output electrical signal, a variable amplifier 204 that amplifies an electrical signal from the integrating amplifier 203, a sample and hold circuit 205 that samples and holds the amplified electrical signal, and a buffer amplifier 206. The integrating amplifier 203 has an operational amplifier that amplifies a read electrical signal and that outputs the amplified signal, an integrating capacitor, and a reset switch. The integrating amplifier 203 is capable of changing an amplification factor by changing the value of the integrating capacitor. The operational amplifier has an inverting input terminal to which an output electrical signal is input, a non-inverting input terminal to which a reference voltage Vref is input from a reference power supply 107b, and an output terminal from which an amplified electrical signal is output. Further, the integrating capacitor is arranged between the inverting input terminal and the output terminal of the operational amplifier. The sample and hold circuit 205 is provided in correspondence with each amplifier circuit, and is constituted by a sampling switch and a sampling capacitor.

Further, the read circuit 103 has a multiplexer 208 that sequentially outputs electrical signals read in parallel from the individual amplifier circuits 207 and that outputs them as image signals of serial signals, and a buffer amplifier 209 that performs impedance conversion on an image signal and that outputs the image signal. An analog image signal Vout output from the buffer amplifier 209 is converted into digital image data by an A/D converter 210 which is then output to the signal processing unit 105, and image data processed by the signal processing unit 105 illustrated in FIG. 1 is output to the control computer 108.

The drive circuit 102 outputs drive signals having a conductive voltage Vcom for bringing a switch element into a conductive state and a non-conductive voltage Vss for bringing a switch element into a non-conduction state in accordance with control signals (D-CLK, OE, DIO) input from the control unit 106 illustrated in FIG. 1 to the individual drive lines. Accordingly, the drive circuit 102 controls the conductive state and non-conductive state of the switch elements, and drives the detection unit 101.

Figure 2:
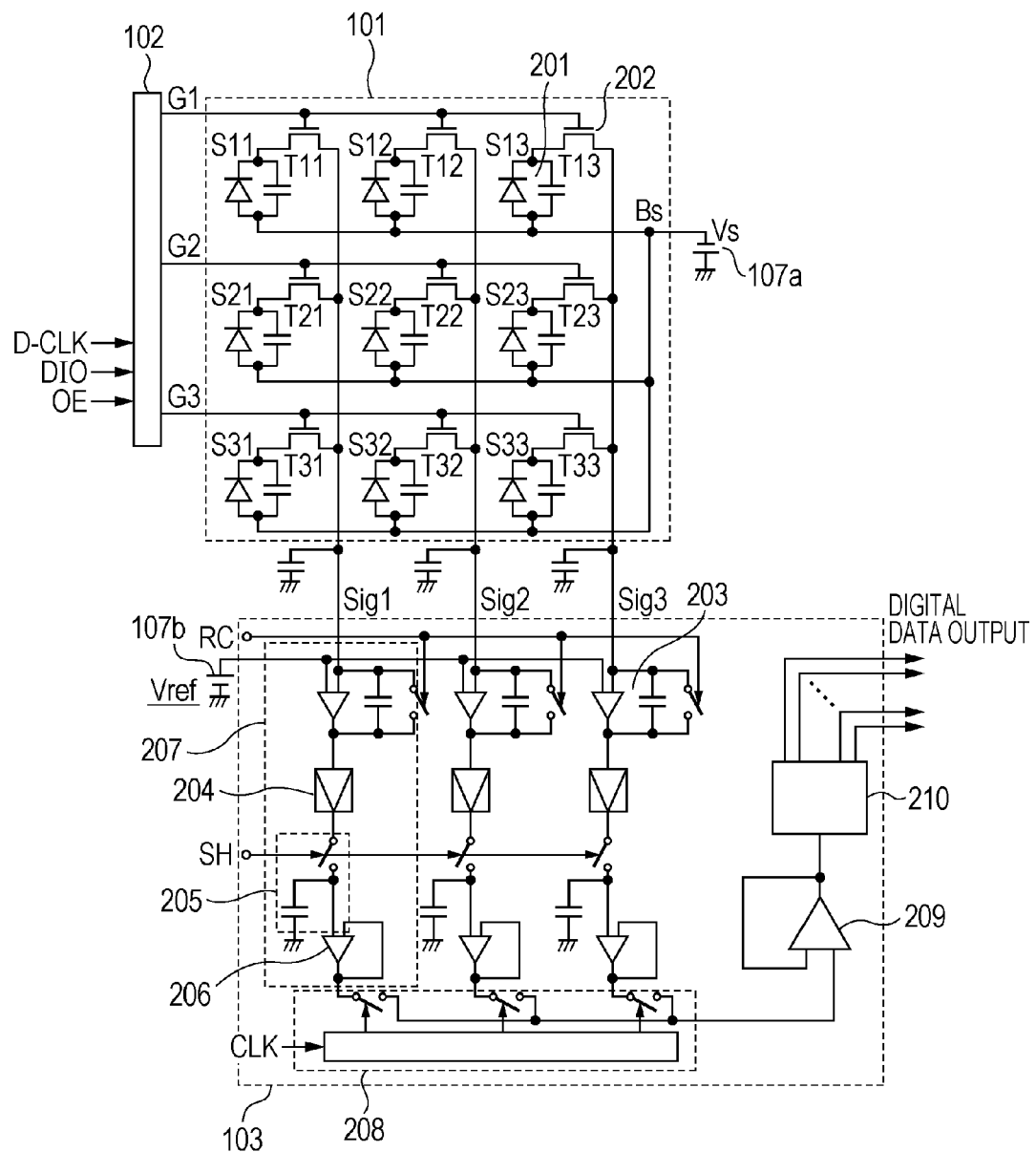
FIG. 2 is a conceptual equivalent circuit diagram of an imaging apparatus according to an embodiment of the present invention.

The power supply unit 107 in FIG. 1 includes the bias power supply 107a and the reference power supply 107b of the amplifier circuits, which are illustrated in FIG. 2. The bias power supply 107a commonly supplies a bias voltage Vs to the other electrode of each conversion element via the bias line Bs. The bias voltage Vs corresponds to a first voltage of the present invention. The reference power supply 107b supplies a reference voltage Vref to the non-inverting input terminal of each operational amplifier. Further, the power supply unit 107 in FIG. 1 further includes a bias-light-source power supply circuit such as an inverter that supplies a voltage required for the operation of the bias light source 115.

The control unit 106 illustrated in FIG. 1 controls the operation of the FPD 104 and the bias light source 115 by receiving a control signal from the control computer 108 or the like outside the apparatus via the signal processing unit 105 and supplying various control signals to the drive circuit 102, the power supply unit 107, and the read circuit 103. The control unit 106 controls the operation of the drive circuit 102 by supplying a control signal D-CLK, a control signal OE, and a control signal DIO to the drive circuit 102. Here, the control signal D-CLK is a shift clock of a shift register used as a drive circuit, the control signal DIO is a pulse transferred by the shift register, and OE is adapted to control an output end of the shift register. Further, the control unit 106 controls the operation of the individual constituent elements of the read circuit 103 by supplying a control signal RC, a control signal SH, and a control signal CLK to the read circuit 103. Here, the control signal RC is adapted to control the operation of the reset switches of the integrating amplifiers, the control signal SH is adapted to control the operation of the sample and hold circuit 205, and the control signal CLK is adapted to control the operation of the multiplexer 208.

Figure 3:
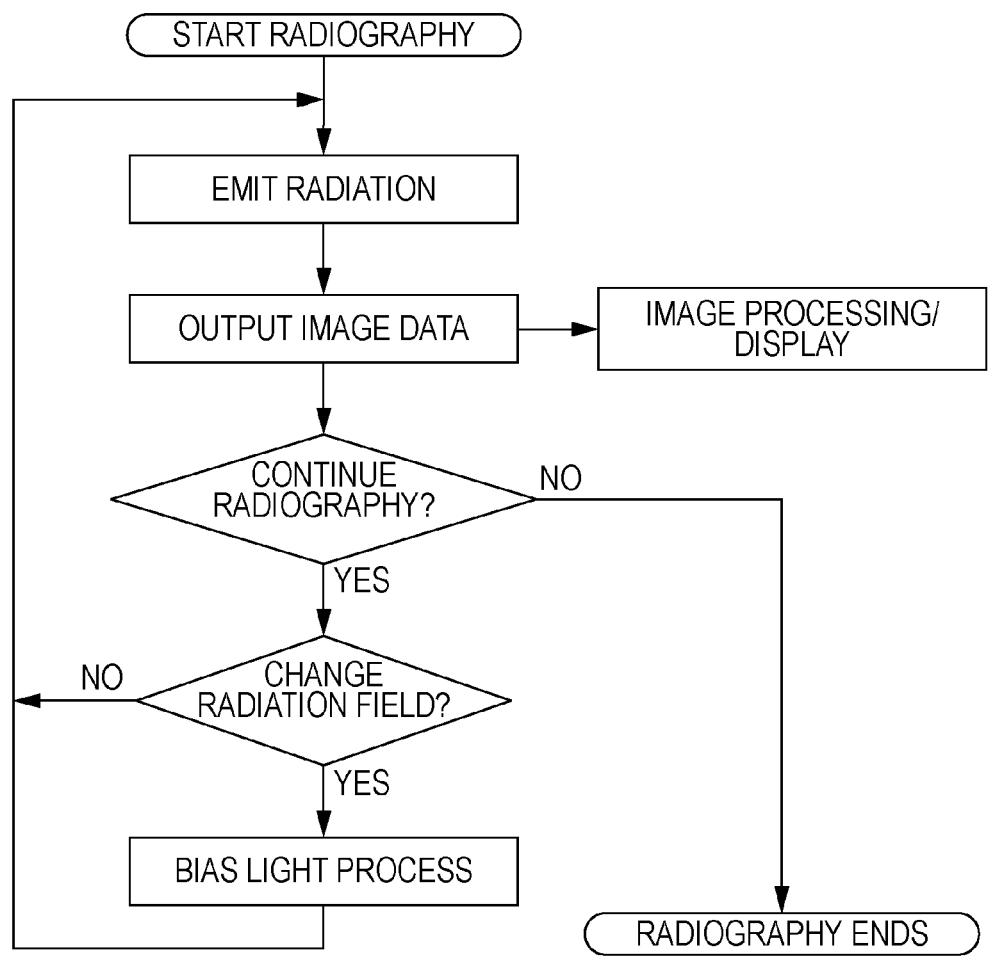
FIG. 3 is a flowchart illustrating the operation of an imaging apparatus and an imaging system according to the present invention.

Next, the overall operation of the imaging apparatus and the imaging system of the present invention will be described with reference to FIGS. 1 to 3, particularly, FIG. 3. In accordance with an operation of the console 114 by an operator, the control computer 108 determines irradiation conditions and starts radiography, and the object is irradiated with desired radiation from the radiation generating device 110 controlled by the radiation control device 109. The imaging apparatus 100 outputs image data corresponding to the radiation transmitted through the object, and the output image data is subjected to image processing by the control computer 108 so that the result is displayed on the display device 113.

The control computer 108 subsequently prompts the operator to confirm whether the continuation of radiography is required or not. When an instruction for the non-continuation of radiography (NO) is received from the operator, the radiography ends. When an instruction for the required continuation of radiography (YES) is received, the operator is prompted to confirm whether the changing of the radiation field is required or not. When an instruction for the non-changing of the radiation field (NO) is received from the operator, the radiation control device 109 and the radiation generating device 110 are controlled under the radiographic conditions previously determined by the control computer 108, and radiation is emitted again under the same conditions. When an instruction for the required changing of the radiation field (YES) is received from the operator, on the other hand, the control computer 108 determines irradiation conditions in which the radiation field has been changed, and the radiation control device 109 controls the radiation field aperture mechanism 112 of the radiation generating device 110 in accordance with the irradiation conditions. Further, the control computer 108 supplies a control signal to the control unit 106 so as to cause the imaging apparatus 100 to perform a bias light process operation described in detail below. After the imaging apparatus 100 has completed the bias light process operation, the control computer 108 controls the radiation control device 109 and the radiation generating device 110 under the irradiation conditions including the changed radiation field, and radiation is emitted under the changed irradiation conditions. Thus, the imaging apparatus 100 performs a next radiographic operation on the changed radiation field.

Figure 4B:
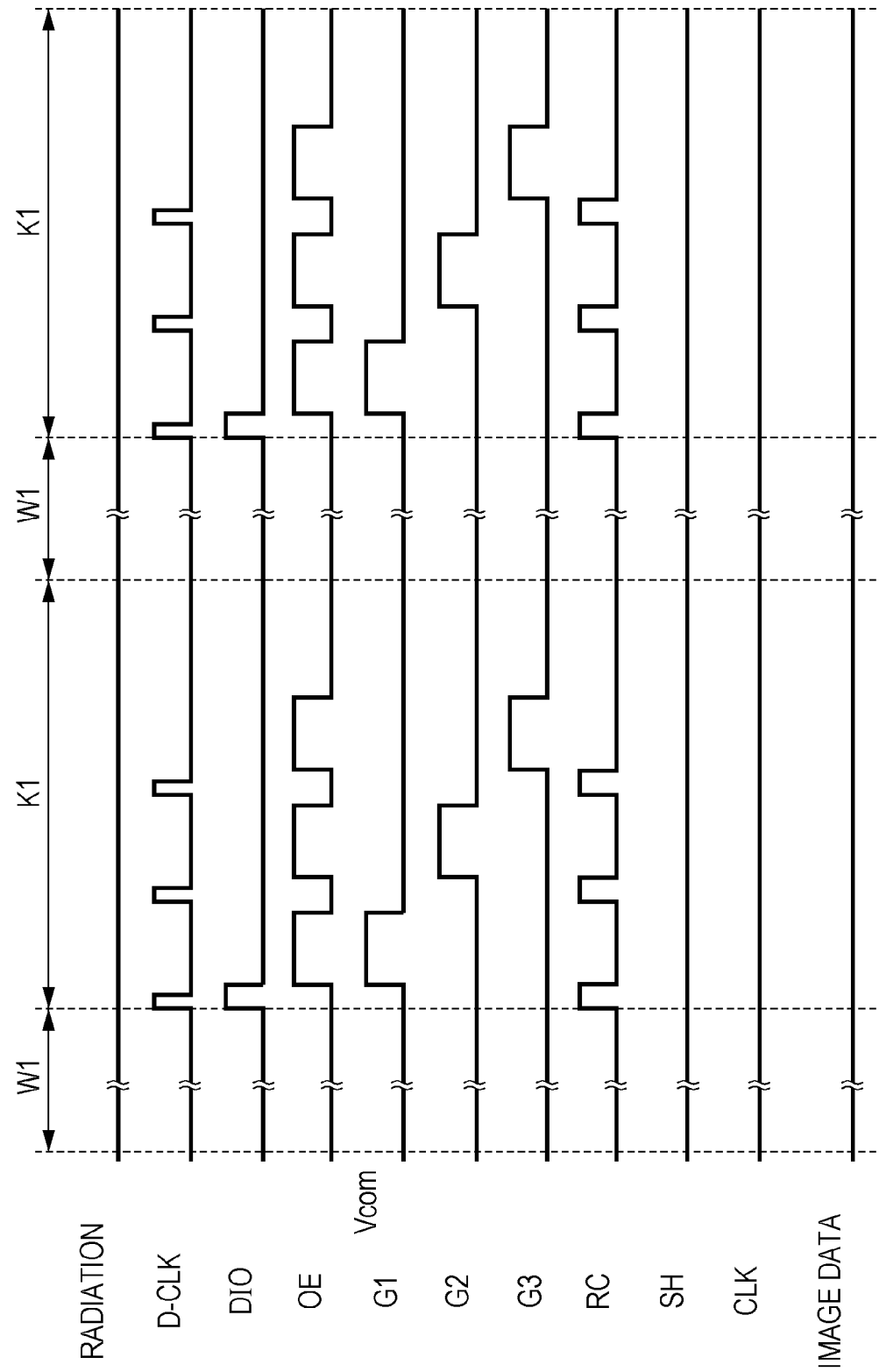
FIG. 4B is a timing chart describing the operation of the imaging apparatus and the imaging system of the present invention.

Next, the operation of the imaging system of the present invention will be described with reference to FIGS. 4A to 4D. In FIG. 4A, when the bias voltage Vs is supplied to the conversion elements 201, the imaging apparatus 100 performs an idling operation during an idling period. Here, the term idling operation is an operation for performing at least an initialization operation K1 repeatedly a plurality of times in order to stabilize the characteristic fluctuation of the detector 104 caused by the start of application of the bias voltage Vs. Further, the term initialization operation is an operation for applying an initial bias before an accumulation operation to the conversion elements and initializing the conversion elements. In FIG. 4A, the operation for performing the set of an accumulation operation W1 and an initialization operation K1 repeatedly a plurality of times is performed as the idling operation.

FIG. 4B is a timing chart describing the operation of the imaging apparatus during a period A-A' in FIG. 4A. As illustrated in FIG. 4B, in the accumulation operation W1, the non-conductive voltage Vss is applied to the switch elements 202 in a state where the bias voltage Vs is applied to the conversion elements 201, and the switch elements of all the pixels are brought into a non-conduction state. In the initialization operation K1, first, the integrating capacitors of the integrating amplifiers and the signal lines are reset by the reset switches, and the conductive voltage Vcom is applied to the drive line G1 from the drive circuit 102 so that the switch elements T11 to T13 of the pixels in the first row are brought into a conductive state. The conductive state of the switch elements allows the conversion elements to be initialized. In this case, the electric charge of the conversion elements is output as electrical signals by the switch elements. In the present embodiment, since the circuits subsequent to the sample and hold circuits are not rendered to operate, the data corresponding to the electrical signals is not output from the read circuit 103. Afterwards, the integrating capacitors and the signal lines are reset again, and thereby the output electrical signals are processed. In this regard, when the above data is used for correction or the like, the circuits subsequent to the sample and hold circuits may be rendered to operate in a manner similar to that of the image output operation or dark image output operation described below. The above control of the conductive state of the switch elements and the above reset are repeatedly performed for the second row and the third row, and thereby the initialization operation of the detector 101 is performed. Here, in the initialization operation, the reset switches may also be kept in a conductive state to continue the reset at least during the conductive state of the switch elements. Further, the conducting time of the switch elements in the initialization operation may be shorter than the conducting time of the switch elements in the image output operation described below. Further, in the initialization operation, switch elements in a plurality of rows may be brought into conduction at the same time. In the above cases, it is possible to reduce the time required for the overall initialization operation, and to more quickly stabilize the characteristic fluctuation of the detector. Note that the initialization operation K1 in the present embodiment is performed during the same period as that of the image output operation included in the fluoroscopic radiography operation performed after the idling operation.

FIG. 4C is a timing chart describing the operation of the imaging apparatus during a period B-B' in FIG. 4A. After the idling operation is performed and the detector is brought into a state where radiography is enabled, in response to a control signal from the control computer 108, the imaging apparatus 100 performs the fluoroscopic radiography operation for irradiating the FPD 104 in the area of the radiation field A with radiation. The fluoroscopic radiography operation corresponds to a first radiography operation of the present invention. Further, the period during which the imaging apparatus 100 performs the fluoroscopic radiography operation is referred to as a fluoroscopic radiography period. During the fluoroscopic radiography period, the imaging apparatus 100 performs the accumulation operation W1 that is performed during a period corresponding to the duration of emission of radiation in order that the conversion elements 201 generate electric charge in accordance with the emitted radiation, and an image output operation X1 for outputting image data on the basis of the electric charge generated in the accumulation operation W1. As illustrated in FIG. 4C, in the image output operation, first, the integrating capacitors and the signal lines are reset, and the conductive voltage Vcom is applied to the drive line G1 from the drive circuit 102 so that the switch elements T11 to T13 in the first row are brought into a conductive state. Accordingly, electrical signals based on the electric charge generated by the conversion elements S11 to S13 in the first row are output to the respective signal lines. The electrical signals output in parallel to the respective signal lines are amplified by the operational amplifiers 203 and variable amplifiers 204 of the corresponding amplifier circuits 207. The sample and hold circuits are caused to operate in response to the control signal SH, and the amplified electrical signals are held in parallel in the sample and hold circuits 205 in the corresponding amplifier circuits. After the electrical signals are held, the integrating capacitors and the signal lines are reset. After the resetting, the conductive voltage Vcom is applied to the drive line G2 in the second row in a manner similar to that in the first row so that the switch elements T21 to T23 in the second row are brought into a conductive state. In the period during which the switch elements T21 to T23 in the second row are brought into a conductive state, the multiplexer 208 sequentially outputs the electrical signals held in the sample and hold circuits 205. Thus, the electrical signals from the pixels in the first row, which are output in parallel, are converted into serial image signals and are then output, and the A/D converter 210 performs conversion to produce image data for one row and then outputs the resulting image data. The above operation is performed for the first to third rows on a row-by-row basis, and thereby image data of one frame is output from the imaging apparatus. Further, in the present embodiment, an accumulation operation W1 that is performed during the same period as that of the accumulation operation W1 in order that the conversion elements 201 generate electric charge in a dark state where no radiation is emitted, and a dark image output operation F1 for outputting dark image data on the basis of the electric charge generated in the accumulation operation W1 are performed. In the dark image output operation F1, an operation similar to the image output operation X1 is performed by the imaging apparatus 100.

Next, when an instruction for changing the radiation field is sent from the console 114 to the control computer 108, the imaging apparatus 100 performs the bias light process operation in accordance therewith. The period during which the bias light process operation is performed is referred to as a bias light process period. The bias light process operation will be described later in detail with reference to FIG. 5.

FIG. 4D is a timing chart describing the operation of the imaging apparatus during a period C-C' in FIG. 4A. After the bias light process operation, the imaging apparatus 100 performs a general (still image) radiography operation for irradiating the FPD 104 with radiation in the radiation field B that is a larger area than the area of the radiation field A. The general radiography operation corresponds to a second radiography operation of the present invention. Further, the period during which the imaging apparatus 100 performs the general radiography operation is referred to as a general radiography period. In the general radiography period, the imaging apparatus 100 performs an accumulation operation W2 that is performed during a period corresponding to the duration of emission of radiation in order that the conversion elements generate electric charge in accordance with the emitted radiation, and an image output operation X2 for outputting image data on the basis of the electric charge generated in the accumulation operation W2. As illustrated in FIG. 4D, here, in the present embodiment, the accumulation operation W2 and the image output operation W2 are operations similar to the accumulation operation W1 and the image output operation W1, respectively, and are represented using different symbols in the present embodiment because the periods of the operations are long. However, the operations may be performed for the same length of time. Further, an accumulation operation W2 that is performed for the same period as that of the accumulation operation W2 prior to the image output operation X2 in order that the conversion elements generate electric charge in a dark state where no radiation is emitted, and a dark image output operation F2 for outputting dark image data on the basis of the electric charge generated in the accumulation operation W2 are performed. In the dark image output operation F2, an operation similar to the image output operation X2 is performed by the imaging apparatus 100. In the present embodiment, furthermore, the imaging apparatus 100 performs an initialization operation K2 prior to each accumulation operation W2. Here, the initialization operation K2 is an operation similar to the initialization operation K1 described previously, and is represented using different symbols in the present embodiment because the period of the operation is long. However, the operation may be performed for the same length of time.

Figure 5A:
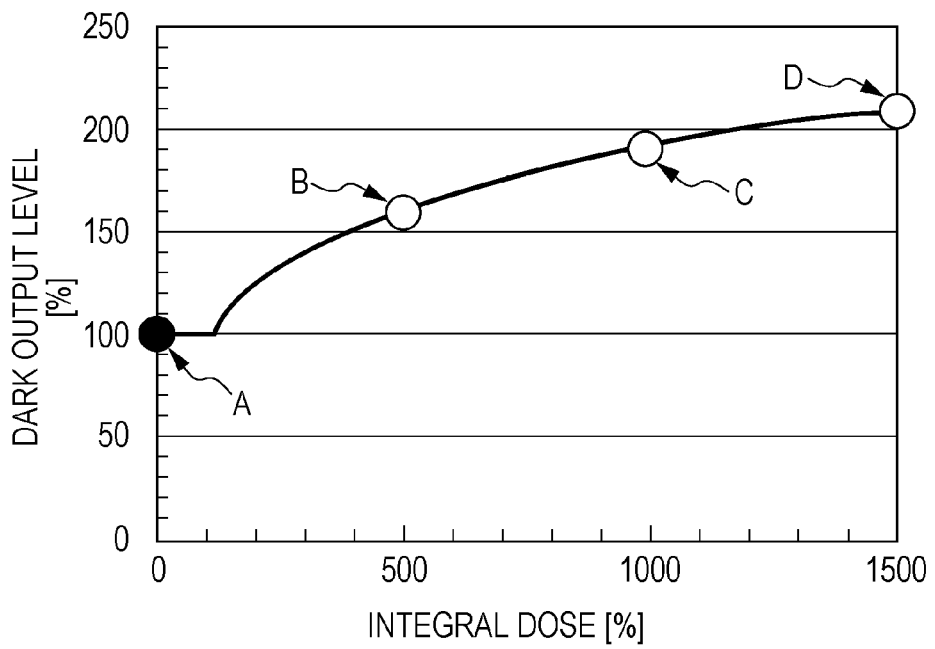
FIG. 5A is a time versus step amount characteristic diagram describing the effect.
Figure 5B:
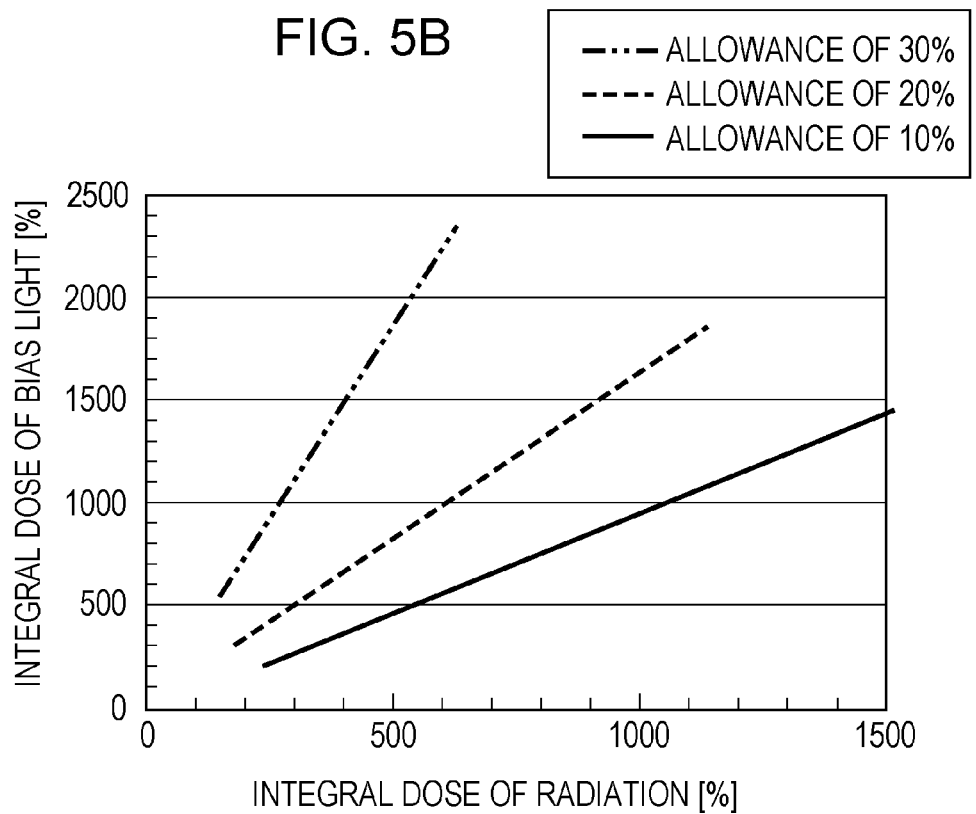
FIG. 5B is a time versus step amount characteristic diagram describing the effect for describing the effect.
Figure 5C:
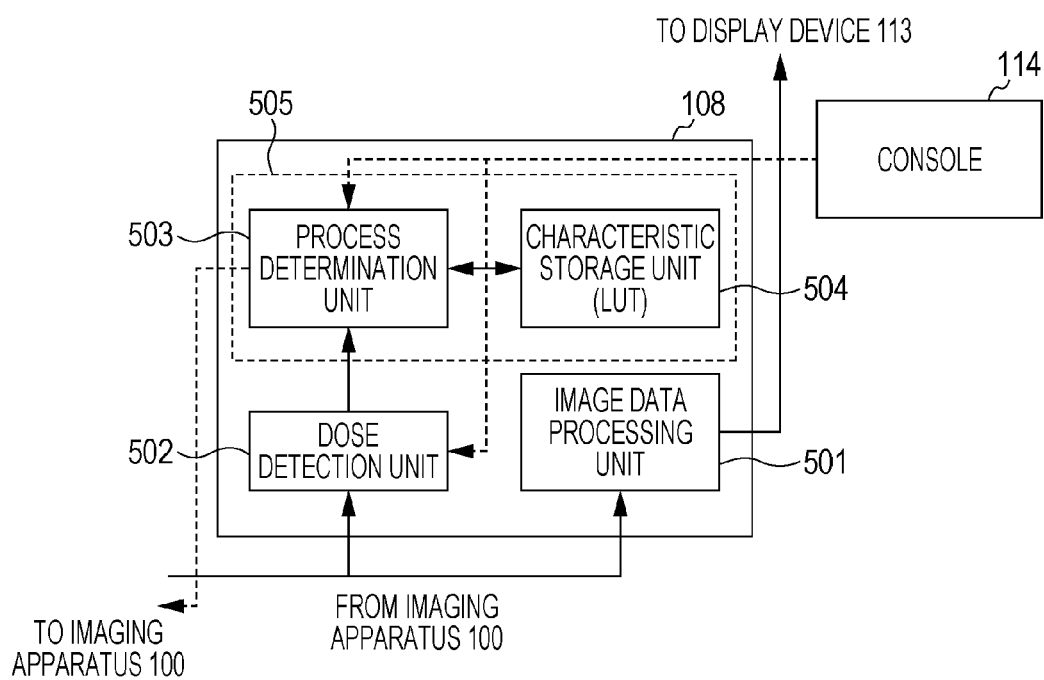
FIG. 5C is a block diagram of a control computer 108.

Next, the mechanism of the occurrence of an image step on which the process of the present invention is based will be described with reference to FIGS. 5A to 5C. In FIGS. 5A to 5C, the abscissa denotes an integral dose of radiation with which the FPD 104 is irradiated. The integral dose is a value standardized with the amount of irradiation with which a conversion element 201 having an integral dose of radiation or bias light of 0 is saturated. In FIG. 5A, the ordinate denotes, as the dark output level, output data of a pixel obtained in a dark state. The dark output level is a level standardized with the dark output level when the integral dose of radiation is 0. In the present embodiment, an area in the detector where the radiation field A is irradiated with radiation is referred to as a first area, and an area other than the first area in an area of the detector where the radiation field B is irradiated with radiation is referred to as a second area.

As illustrated in FIG. 5A, the inventor of the claimed invention has found that the dark output of a flat panel detector depends upon the history of emission of radiation, more specifically, depends upon the integral dose of radiation after a bias voltage is applied to a conversion element of the flat panel detector. In the present embodiment, since a radiography operation is performed on the radiation field A, the dark output of the pixels included in the second area is represented by A in FIG. 5A, and the dark output of the pixels included in the first area is represented by B to D. Further, the dark output of the pixels included in the first area exhibits B to D in FIG. 5A dependently on the integral dose that depends upon the length of the period of the fluoroscopic radiography operation. Thus, for example, when the integral dose of radiation in the fluoroscopic radiography operation is 500%, a difference of approximately 60% occurs between the dark output A for the second area and the dark output B for the first area, and the difference in dark output yields an image step. In particular, the longer the period of the fluoroscopic radiography operation is, the larger the difference in dark output between the first area and the second area is, resulting in more noticeable step in the image. In this manner, the inventor of the claimed invention has found that since the dark output of a flat panel detector depends upon the history of emission of radiation, a difference in dark output occurs between the area irradiated with radiation and the non-irradiated area in the flat panel detector, thus causing an image step.

From the characteristics illustrated in FIG. 5A, the inventor of the claimed invention has found that the occurrence of an image step can be reduced by using the following bias light process operation. In accordance with a change from the radiation field A to the radiation field B, the bias light source 115 irradiates the flat panel detector 104 with bias light on the basis of information regarding the integral dose of radiation in the first radiography operation during the period between the first radiography operation and the second radiography operation. Thus, the control computer 108 determines the integral dose of bias light on the basis of information regarding the integral dose of radiation in the first radiography operation. Then, the control computer 108 supplies a control signal based on the determined integral dose of bias light to the control unit 106. Upon receipt of the control signal, the control unit 106 controls the operation of the bias light source 115 on the basis of the control signal.

Here, an examination will be made of the dark output, as A in FIG. 5A, of the pixels included in the second area when the radiation field is changed and the dark output, as B, of the pixels included in the first area. In this case, the difference in dark output level between both pixels, which is caused by an image step, is 60%. Then, the second area is selectively irradiated with bias light at an integral dose of 500% to perform the bias light process operation. Therefore, the dark output of the pixels included in the second area immediately before the second radiography operation is performed becomes B, and the dark output level of the pixels included in the first area becomes substantially equivalent to that of the pixel included in the second area. This reduces the difference in dark output between both areas in the second radiography operation, and reduces the influence of the image step.

However, if the accuracy of selective irradiation with bias light is insufficient, there is a risk that a pixel located adjacent to the second area among the pixels included in the first area may be irradiated with bias light. In this case, this pixel is irradiated with radiation or light at an integral dose of approximately 1000% in total, and the dark output level immediately before the second radiography operation is performed becomes C in FIG. 5A. However, since the dark output level of the pixels included in the second area becomes B, the difference in dark output level between both pixels is up to approximately 30%, which is half that before the bias light process operation.

Further, the integral dose of bias light with which the second area is selectively irradiated may not necessarily match the integral dose of radiation with which the first area is irradiated in the first radiography operation. For example, when the pixels included in the second area are selectively irradiated at an integral dose of 400%, the difference in dark output level between the pixels included in the second area and the pixels included in the first area is reduced to approximately 10%. If the above differences are allowable differences in dark output level, no image step is visually perceived in the obtained image data. If the difference in dark output level is less than or equal to 30%, an image step that is less than or equal to 1/10 that of the effective value of random noise in the image data is obtained, and the image step is not visually recognized, which is obtained from the result of an experiment. In this manner, the inventor of the claimed invention has found that the bias light process operation is performed so that the difference can be less than or equal to a predetermined allowable difference in dark output level, and thereby image data with reduced image steps can be obtained. The determined allowable difference in dark output level is hereinafter referred to as an allowance.

When selective emission of bias light is performed, preferably, an LED array having a plurality of LED elements arranged in a matrix is used as a bias light source. The LED array is provided with a selectably operable driver, and is configured to be capable of selectively emitting light in accordance with the second area. Thus, the driver is costly, and the complexity of control of the driver and the LED array is increased.

Furthermore, in the bias light process operation, both the first and second areas may be irradiated with bias light. Again, an examination will be made of the dark output, as A in FIG. 5A, of the pixels included in the second area when the radiation field is changed and the dark output, as B, of the pixels included in the first area. Both the first and second areas are irradiated with bias light at an integral dose of 500% to perform the bias light process operation. Therefore, the dark output of the pixels included in the first area becomes C in FIG. 5A, and the dark output level of the pixels included in the second area becomes B. The difference in dark output level between both pixels is thus up to approximately 30%, which is half that before the bias light process operation. If the irradiation with bias light at an integral dose of 500% is further performed and the irradiation with bias light at 1000% is performed in total, the dark output of the pixels included in the first area becomes D in FIG. 5A, and the dark output level of the pixels included in the second area becomes C. The difference in dark output level between both pixels is therefore up to approximately 20%, and a further reduction is provided. If the above differences are less than or equal to the allowance, it is difficult to visually perceive an image step in the obtained image data. If the difference in dark output level is less than or equal to 30%, an image step that is less than or equal to $1/10$ that of the effective value of random noise in the image data is obtained, and the image step is not visually recognized, which is obtained from the result of an experiment. In this manner, the inventor of the claimed invention has found that the bias light process operation is performed so that the difference can be less than or equal to a predetermined allowance, and thereby image data with reduced image steps can be obtained.

FIG. 5B is a graph illustrating the relationship between the integral dose of radiation in the first radiography operation and the integral dose of bias light in the bias light process operation with respect to individual allowances. In FIG. 5B, the ordinate denotes a value standardized with the amount of irradiation at which a conversion element 201 having an integral dose of radiation or bias light of 0 is saturated. This figure illustrates the case where the first and second areas are irradiated with bias light. The inventor of the claimed invention has found that, as illustrated in FIG. 5B, when individual allowances are determined and if the integral dose of radiation in the first radiography operation is defined, the integral dose of bias light emitted in the bias light process operation is determined.

Next, a configuration for performing an arithmetic process of the present invention and a specific arithmetic process will be described with reference to FIG. 5C. The control computer 108 has an image data processing unit 501, a dose detection unit 502, a process determination unit 503, and a characteristic storage unit 504. Here, the characteristic storage unit 504 stores data regarding, as illustrated in FIG. 5B, the integral dose of radiation in the first radiography operation, allowances, and the required integral dose of bias light. A lookup table storing the above data is suitably used as the characteristic storage unit 504. In the present invention, a section including the process determination unit 503 and the characteristic storage unit 504 is referred to as an arithmetic processing unit 505.

Image data output from the imaging apparatus 100 is subjected to image processing by the image data processing unit 501, and is transmitted to the display device 113. In the image data, image data corresponding to the pixels included in the first area is transmitted as dose detection data to the dose detection unit 502. The dose detection unit 502 determines a dose of radiation per frame on the basis of the dose detection data, and accumulates the doses of radiation. Here, image data corresponding to a specific pixel included in the first area, or an average value of image data output from the plurality of pixels included in the first area may be used as the dose detection data. Alternatively, in place of image data, data from a photo-timer (not illustrated) provided separately from the detection unit in the imaging apparatus may be used. The dose detection unit 502 determines the sum of doses of radiation in units of one frame, which are accumulated, on a frame-by-frame basis, and creates information regarding the integral dose in the radiography operations. Further, information regarding the integral dose of radiation in the first radiography operation may be created based on information about radiographic conditions in the first radiography operation which are obtained from the console 114. The dose detection unit 502 outputs the created information regarding the integral dose to the process determination unit 503.

Then, the process determination unit 503 determines the integral dose of bias light in the bias light process operation on the basis of the information regarding the integral dose of radiation which is output from the dose detection unit 502 and the information regarding the integral dose of bias light which is stored in the characteristic storage unit 504. Then, the arithmetic processing unit 505 applies a control signal corresponding to the determined integral dose of bias light to the control unit 106 of the imaging apparatus 100. In response to the control signal, the control unit 106 controls the operation of the bias light source 115 on the basis of the control signal. In the present embodiment, the control computer 108 determines a process. However, the present invention is not limited thereto. In response to a control signal from the control computer, the control unit 106 of the imaging apparatus 100 may determine a process.

Figure 5D:
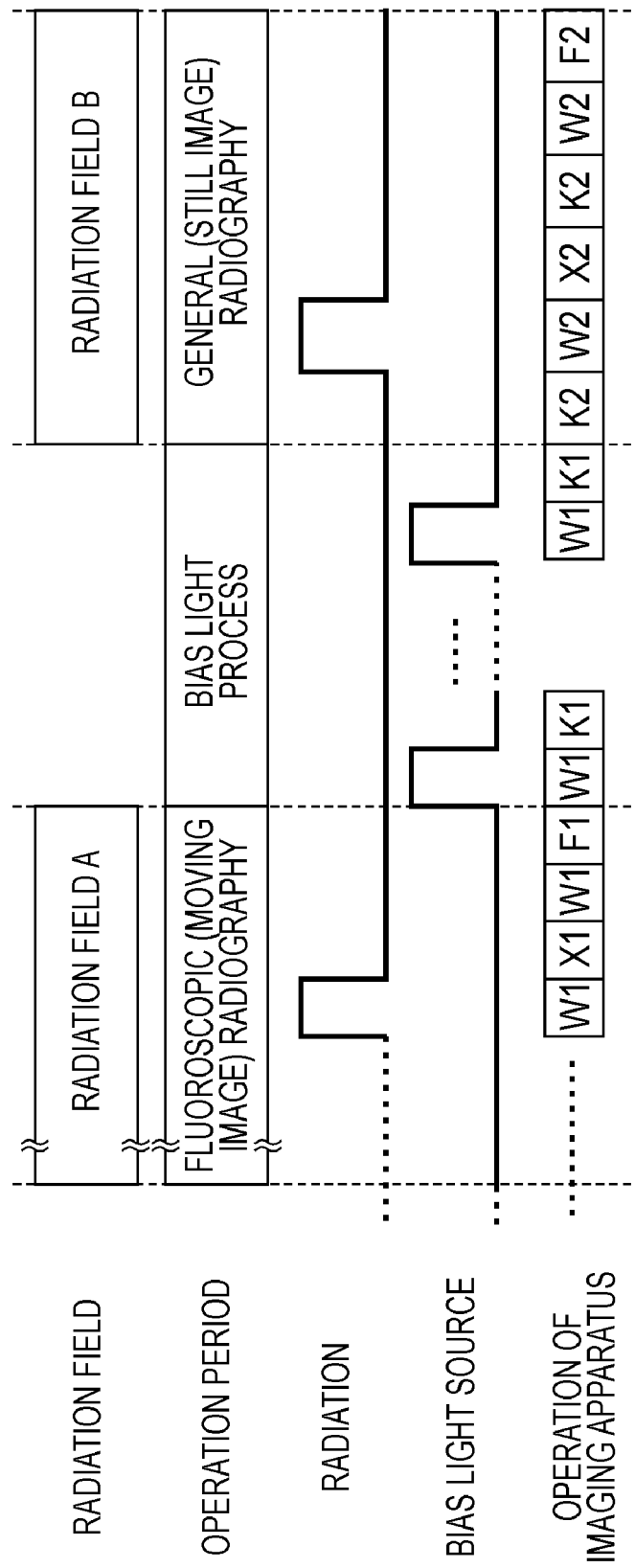
FIG. 5D is a timing chart describing a changing operation of the present invention.
Figure 5E:
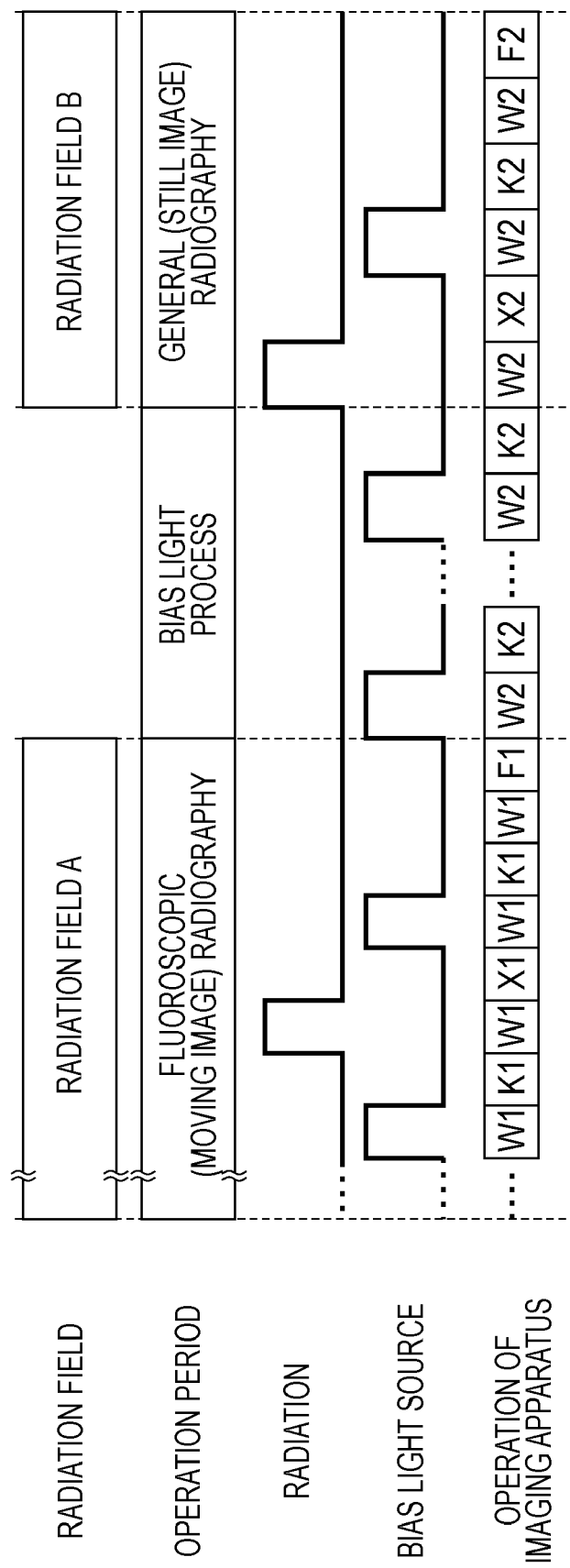
FIG. 5E is a timing chart describing a changing operation of the present invention.

Next, the bias light process operation of the present embodiment will be described with reference to FIGS. 5D to 5E. In the bias light process operation of the present invention, the bias light source 115 irradiates the FPD 104 with bias light. Then, after irradiated with bias light, the FPD 104 performs the operation for initializing the conversion elements. Further, it has been found that the set of operations of emitting bias light and initializing the conversion elements is performed a plurality of times, resulting in a greater improvement in the step reduction effect. The bias light process operation in which such a set of operations of emitting bias light and initializing the conversion elements is performed once or a plurality of times can prevent reduction in image quality which is caused by an image step that can occur in an obtained image in accordance with a change of the radiation field.

In the bias light process operation illustrated in FIG. 5D, the bias light source 115 performs emission of bias light in addition to emission of radiation in the fluoroscopic radiography operation that is performed before a change of the radiation field, which has been described with reference to FIG. 4C. Then, the FPD 104 performs the set of the accumulation operation W1 and the initialization operation K1 in the fluoroscopic radiography operation once or a plurality of times. That is, the FPD 104 performs the set of the accumulation operation W1 and the initialization operation K1 corresponding to the fluoroscopic radiography operation that is performed after the change of the radiation field once or a plurality of times. In the bias light process operation of FIG. 5D, the time required for the operation is reduced, and the usability of the apparatus is further improved. However, if the initialization operation that is performed in the bias light process operation does not correspond to the radiography operation after the change of the radiation field and is performed for a length of time different from that of the initialization operation that is performed in the radiography operation after the change of the radiation field, there is a risk that the characteristic stability of the conversion elements in the accumulation operation in the radiography operation may be reduced. Thus, there is a risk that image data containing many artifacts may be obtained.

In the changing operation illustrated in FIG. 5E, the bias light source 115 performs emission of bias light in synchronization with emission of radiation in the general radiography operation that is performed after the change of the radiation field, which has been described with reference to FIG. 4D. Then, the FPD 104 performs the set of the accumulation operation W2 and the initialization operation K2 in the general radiography operation that is performed after the change of the radiation field once or a plurality of times. That is, the FPD 104 performs the set of the accumulation operation W2 and the initialization operation K2 corresponding to the general radiography operation that is performed after the change of the radiation field once or a plurality of times. In this manner, the changing operation is performed in synchronization with the operation included in the operation prior to the image output operation in the radiography operation performed after the change, thus making the characteristics of the conversion elements stable in the accumulation operation W2 in the radiography operation. Therefore, good image data with a small number of artifacts can be obtained. In FIG. 5E, furthermore, in the fluoroscopic radiography operation, prior to the set of the accumulation operation W1 and the image output operation X1 and the set of the accumulation operation W1 and the dark image output operation F1, the emission of bias light in synchronization with the accumulation operation W1 and the initialization operation K1 are performed. In addition, in the general radiography operation, prior to the set of the accumulation operation W2 and the dark image output operation F2, the emission of bias light in synchronization with the accumulation operation W2 and the initialization operation K2 are performed. In particular, in the general radiography operation, the emission of bias light in the bias light process operation and the initialization operation K2 are performed prior to the emission of radiation. Therefore, the emission of bias light and the initialization operation K2 are performed prior to the set of the accumulation operation W2 and the dark image output operation F2, thus allowing the set of operations including the accumulation operation W2 and the image output operation F1 to be synchronized with the set of operations including the accumulation operation W2 and the dark image output operation F2. Therefore, the influences of dark output on the image data of radiation and the dark image data can be mixed together, and good image data with a smaller number of artifacts can be obtained.

In this manner, the bias light process operation is performed before the radiography operation after the change of the radiation field is started. This enables a reduction in the occurrence of ghosts (image steps) affected by a radiation area, which can occur in an obtained image, and avoidance of a significant reduction in image quality without complex image processing being performed.

Figure 6A:
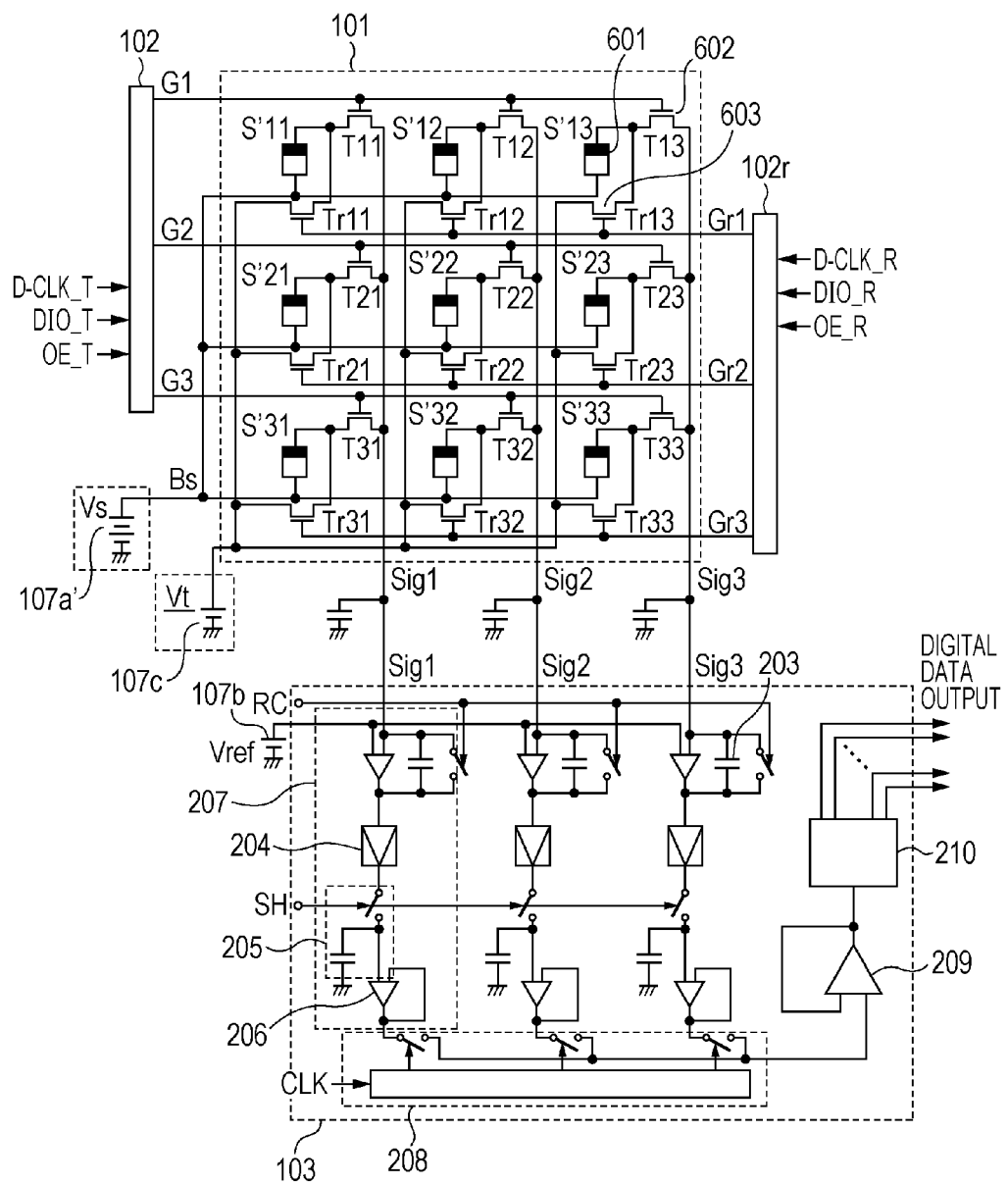
FIG. 6A is a conceptual equivalent circuit diagram of another imaging apparatus according to the present invention.
Figure 6B:
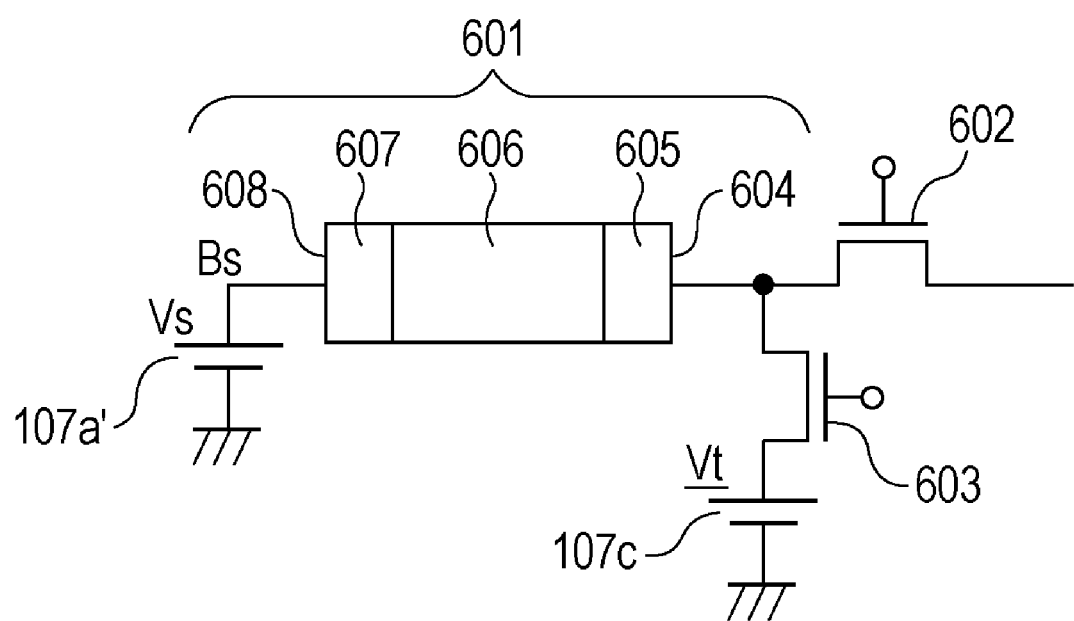
FIG. 6B is a conceptual equivalent circuit diagram of another imaging apparatus according to the present invention.

While in the present embodiment, PIN-type photodiodes are used as the conversion elements 201, the present invention is not limited thereto. As illustrated in FIGS. 6A and 6B, an imaging apparatus that includes a pixel having a conversion element 601 using an MIS-type photoelectric conversion element as an MIS-type conversion element and including a refresh switch element 603 in addition to an output switch element 602 may be used. Here, in FIG. 6A, one of main terminals of the refresh switch element 603 is electrically connected to a first electrode 604 of the conversion element 601 and one of two main terminals of the switch element 602. Further, the other main terminal of the switch element 603 is electrically connected to a refresh power supply 107c incorporated in the power supply unit 107 via a common line. A plurality of switch elements 603 in the row direction have control terminals that are commonly electrically connected to refresh drive lines Gr, and drive signals are applied from a refresh drive circuit 102r via the refresh drive lines Gr on a row-by-row basis. Further, as in FIG. 6B, the conversion element 601 is provided with a semiconductor layer 606 between the first electrode 604 and a second electrode 608, an insulating layer 605 between the first electrode 604 and the semiconductor layer 606, and an impurity semiconductor layer between the semiconductor layer 606 and the second electrode 608. The second electrode 608 is electrically connected to a bias power supply 107a' via a bias line Bs. In the conversion element 601, similarly to the conversion element 201, a bias voltage Vs is supplied from the bias power supply 107a' to the second electrode 608, and a reference voltage Vref is supplied to the first electrode 604 via the switch element 602. Then, an accumulation operation is performed. Here, in the fluoroscopic and general radiography operations, a refresh voltage Vt is supplied to the first electrode 604 via the switch element 603, and the conversion element 601 is refreshed by a bias |Vs−Vt| thereof. Elements having the same configuration as that of FIG. 2 are assigned the same numerals, and detailed descriptions thereof are omitted.

Figure 7B:
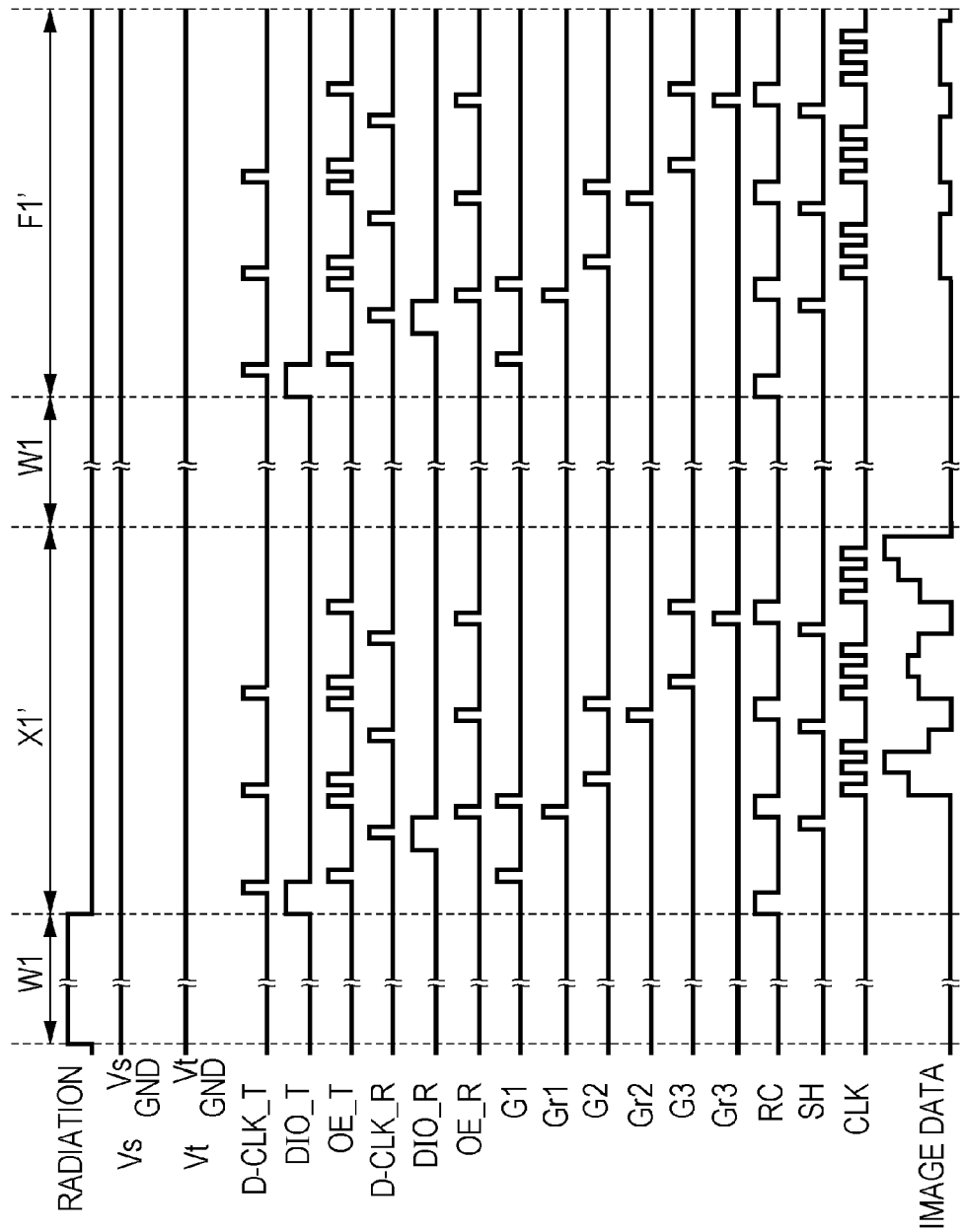
FIG. 7B is a timing chart describing the operation of the other imaging apparatus and imaging system according to the present invention.

FIGS. 7A to 7C illustrate the operation of the imaging apparatus of FIG. 6. FIG. 7A is a timing chart describing the operation of the imaging apparatus during the period A-A' in FIG. 4A. FIG. 7B is a timing chart describing the operation of the imaging apparatus during the period B-B' in FIG. 4A. FIG. 7C is a timing chart describing the operation of the imaging apparatus during the period C-C' in FIG. 4A. In place of the initialization operation K1, the image output operation X1, and the dark image output operation F1 in the first embodiment illustrated in FIG. 4A, an initialization operation K1', an image output operation X1', and a dark image output operation F1' are performed, respectively. Further, in place of the image output operation X2 and the dark image output operation F2 in the first embodiment illustrated in FIG. 4A, an image output operation X2' and a dark image output operation F2' are performed, respectively. Other operations are similar to those in FIG. 4A, and detailed descriptions thereof are omitted.

Embodiments of the present invention can also be implemented by executing a program by, for example, a computer included in the control unit 106. Further, means for supplying the program to the computer, for example, computer-readable recording media such as a CD-ROM on which the program is recorded, or transmission media such as the Internet that carry the program, can also be applied as embodiments of the present invention. Further, the above program can also be applied as an embodiment of the present invention. The above program, recording media, transmission media, and program product fall within the scope of the present invention. Further, an invention based on the combination of features that can be easily conceived from the present embodiments also falls within the scope of the present invention.

According to the claimed invention, it is possible to reduce the occurrence of a ghost (image step) affected by a radiation area, which occurs in an obtained image, by the driving operation of an FPD, without performing complex image processing, and to avoid significant reduction in image quality.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST 100 imaging apparatus
101 detection unit
102 drive circuit
103 read circuit
104 flat panel detector
105 signal processing unit
106 control unit
107 power supply unit
108 control computer
109 radiation control device
110 radiation generating device
111 radiation source
112 radiation field aperture mechanism
113 display device 114 console
115 bias light source

The invention claimed is:

1. A radiographic imaging system comprising:
an imaging apparatus including,
a detector configured to be irradiated with radiation incident on a first radiation field thereof and with radiation incident on a second radiation field thereof larger than the first radiation filed, the detector having a plurality of pixels arranged in a matrix, the pixels having conversion elements that convert the radiation incident on the detector into an electric charge, the detector being configured to perform a first radiography operation for outputting image data corresponding to the radiation with which the first radiation field is irradiated, and a second radiography operation for outputting image data corresponding to the radiation with which the second radiation field is irradiated,
a light source that irradiates the detector with light separate from the radiation, and
a control unit configured to control an operation of the detector including the first radiography operation and the second radiography operation,
said control unit further configured to control the light source to irradiate the detector with the light; and
a control computer configured to control the imaging apparatus,
wherein the control computer further configured to determine an amount of light with which the light source irradiates the detector based on a dose of radiation used to irradiate the first radiation field of the detector in the first radiography operation, and applies a control signal to the control unit based on the determined amount of light, and
wherein the control unit further configured to control the light source so that, in response to a change from the first radiography operation to the second radiography operation the light source irradiates the detector with the determined amount of light during a period between the first radiography operation and the second radiography operation.

2. The imaging system according to claim 1, wherein the control unit controls the detector so that the detector performs an initialization operation for initializing the conversion elements after the irradiation with the light.

3. The imaging system according to claim 2, wherein the control unit controls the detector and the light source so that the irradiation with the light and the initialization operation are performed a plurality of times.

4. The imaging system according to claim 2, wherein the pixels further include switch elements for outputting electrical signals corresponding to the electric charge, and
wherein the detector includes a detection unit in which the plurality of pixels are arranged, a drive circuit that controls a conductive state of the switch elements in order to drive the detection unit, and a read circuit that outputs, as the image data, the electrical signals which are output from the detection unit via signal lines connected to the switch elements,
wherein the read circuit includes a reset switch that resets the signal lines, and
wherein the control unit controls the drive circuit and the reset switch so that the detector performs the initialization operation for initializing the conversion elements after the irradiation with the light.

5. The imaging system according to claim 4, wherein the conversion elements include photoelectric conversion elements and a wavelength converter which converts radiation into light of a wavelength band detectable by the photoelectric conversion element, and the photoelectric conversion elements are PIN-type photodiodes.

6. The imaging system according to claim 2, wherein the conversion elements are MIS-type conversion elements, each of the MIS-type conversion elements having a first electrode, a second electrode, a semiconductor layer arranged between the first electrode and the second electrode, an insulating layer arranged between the first electrode and the semiconductor layer, and an impurity semiconductor layer arranged between the semiconductor layer and the second electrode,
wherein the pixels further include switch elements for outputting electrical signals corresponding to the electric charge, and other switch elements different from the switch elements,
wherein the detector includes a detection unit in which the plurality of pixels are arranged, a drive circuit that controls a conductive state of the switch elements in order to drive the detection unit, and a read circuit that outputs, as the image data, the electrical signals which are output from the detection unit via signal lines connected to the switch elements, another drive circuit that controls a conductive state of the other switch elements, and a power supply unit including a reference power supply that applies a reference voltage to the first electrode of each of the conversion elements via the corresponding one of the switch elements, a refresh power supply that applies a refresh voltage to the first electrode via the corresponding one of the other switch elements, and a bias power supply that applies a bias voltage to the second electrode of each of the conversion elements, and
wherein the detector refreshes the conversion elements by maintaining the switch elements in a non-conductive state while bringing the other switch elements into a conductive state and by applying the bias voltage to the second electrodes while applying the refresh voltage to the first electrodes via the other switch elements.

7. The imaging system according to claim 6, wherein the MIS-type conversion elements include MIS-type photoelectric conversion elements and a wavelength converter which converts radiation into light of a wavelength band detectable by the MIS-type photoelectric conversion elements.

8. The imaging system according to claim 1, wherein the detector includes a first area irradiated with radiation in the first radiation field, and a second area other than the first area in an area of the detector which is irradiated with radiation in the second radiation field, and
wherein the light source selectively irradiates the second area with the determined amount of light during the period between the first radiography operation and the second radiography operation.

9. The imaging system according to claim 1, wherein the detector includes a first area irradiated with radiation in the first radiation field, and a second area other than the first area in an area of the detector which is irradiated with radiation in the second radiation field, and
wherein the light source irradiates the first and second areas with the determined amount of light during the period between the first radiography operation and the second radiography operation.

10. The radiographic imaging system according to claim 1, further comprising a console that outputs information on a radiographic condition in the first radiography operation to the control computer,
wherein the control computer includes a storage unit, a dose detection unit, and a process determination unit, wherein the storage unit stores information regarding the amount of light determined, wherein the dose detection unit outputs information regarding the dose of radiation in the first radiography operation, which is created on the basis of the information on the radiographic condition in the first radiography operation, to the process determination unit, and wherein the process determination unit determines the amount of light based on the information regarding the dose of radiation which is output from the dose detection unit.

11. The radiographic imaging system according to claim 1, wherein the control computer includes a storage unit, a dose detection unit, and a process determination unit, wherein the storage unit stores information regarding the amount of light determined, wherein the dose detection unit outputs information regarding the dose of radiation in the first radiography operation, which is determined using the image data or data from a photo-timer provided separately from the detector, to the process determination unit, wherein the process determination unit determines the amount of light based on the dose of radiation which is output from the dose detection unit.

12. The imaging system according to claim 1, further comprising:
  a radiation source configured to generate the radiation to be incident on the detector; and
  a radiation field aperture mechanism configured to control a size of the first radiation field and a size of the second radiation field,
  wherein a first area of the detector irradiated by the radiation during the first radiographic operation corresponds to the size of first radiation field, and a second area of the detector larger than the first area irradiated during the second radiographic operation corresponds to the size of the second radiation field.

13. A method for performing radiographic imaging comprising:
  a radiation exposure step of irradiating a detector with radiation incident on a first radiation field thereof and with radiation incident on a second radiation field thereof larger than the first radiation field, the detector having a plurality of pixels arranged in a matrix, the pixels having conversion elements that convert the radiation incident on the detector into an electric charge;
  a control step of controlling an operation of the detector to selectively perform an operation including a first radiography operation for outputting image data corresponding to the radiation with which the first radiation field is irradiated and a second radiography operation for outputting image data corresponding to the radiation with which the second radiation field is irradiated;
  a determination step of determining an amount of light with which to irradiate the detector based on a dose of radiation used to irradiate the first radiation field of the detector in the first radiography operation; and
  a light exposure step of irradiating the detector with light different from the radiation in response to a change in the operation of the detector from the first radiography operation to the second radiography operation, wherein the second radiation field of the detector is irradiated with the determined amount of light during a period between the first radiography operation and the second radiography operation.

14. A non-transitory computer-readable medium storing thereon a computer-executable program for causing a computer to execute control of an imaging apparatus, the program causing the computer to execute processing steps comprising:
  a radiation exposure step of irradiating a detector with radiation incident on a first radiation field thereof and with radiation incident on a second radiation field thereof larger than the first radiation field, the detector having a plurality of pixels arranged in a matrix, the pixels having conversion elements that convert the radiation incident on the detector into an electric charge;
  a control step of controlling the detector to selectively perform an operation including a first radiography operation for outputting image data corresponding to radiation with which the first radiation field is irradiated and a second radiography operation for outputting image data corresponding to the radiation with which the second radiation field is irradiated;
  a determination step of determining an amount of light with which to irradiate the detector based on a dose of radiation used to irradiate the first radiation field of the detector in the first radiography operation,
  a light exposure step of irradiating the detector with light different from the radiation in response to a change in the operation of the detector from the first radiography operation to the second radiography operation, wherein the second radiation field of the detector is irradiated with the determined amount of light during a period between the first radiography operation and the second radiography operation.

\* \* \* \* \*